US008358418B2

(12) United States Patent
Myrick et al.

(10) Patent No.: US 8,358,418 B2
(45) Date of Patent: *Jan. 22, 2013

(54) OPTICAL ANALYSIS SYSTEM FOR DYNAMIC REAL-TIME DETECTION AND MEASUREMENT

(75) Inventors: Michael L. Myrick, Irmo, SC (US); Robert P. Freese, Pittsboro, NC (US); Ryan J. Priore, Columbia, SC (US); John C. Blackburn, Charleston, SC (US); Jonathan H. James, Columbia, SC (US); David L. Perkins, Irmo, SC (US)

(73) Assignee: Halliburton Energy Services, Inc., Houston, TX (US)

( * ) Notice: Subject to any disclaimer, the term of this patent is extended or adjusted under 35 U.S.C. 154(b) by 432 days.

This patent is subject to a terminal disclaimer.

(21) Appl. No.: 12/094,465

(22) PCT Filed: Mar. 10, 2006

(86) PCT No.: PCT/US2006/008972
§ 371 (c)(1),
(2), (4) Date: Oct. 3, 2008

(87) PCT Pub. No.: WO2007/061437
PCT Pub. Date: May 31, 2007

(65) Prior Publication Data
US 2009/0219539 A1  Sep. 3, 2009

Related U.S. Application Data

(60) Provisional application No. 60/740,054, filed on Nov. 28, 2005, provisional application No. 60/773,276, filed on Feb. 14, 2006.

(51) Int. Cl.
*G01N 21/55* (2006.01)

(52) U.S. Cl. ........ 356/445; 356/419; 356/310; 356/319; 356/301; 356/369

(58) Field of Classification Search .................. 356/445, 356/419, 310, 319, 301, 367
See application file for complete search history.

(56) References Cited

U.S. PATENT DOCUMENTS
3,717,078 A  2/1973  Ogura
(Continued)

FOREIGN PATENT DOCUMENTS
EP  57142546 A  9/1982
(Continued)

OTHER PUBLICATIONS

M.L. Myrick et al., "Application of Multivariate Optical Computing to Near-Infrared Imaging", Vibration Spectroscopy-based Sensor System, Proceedings of SPIE, vol. 4577, pp. 148-157, 2002.

(Continued)

*Primary Examiner* — Tarifur Chowdhury
*Assistant Examiner* — Isiaka O Akanbi
(74) *Attorney, Agent, or Firm* — Haynes and Boone, LLP

(57) ABSTRACT

A method of real-time processing and monitoring comprises the steps of blending a material of interest (e.g., an active pharmaceutical material), with a secondary material, (e.g., an excipient), illuminating the blended materials with light, reflecting light carrying information about the blended materials through at least one multivariate optical element (148) and detecting said light with a first detector (152), detecting a deflected portion of the information carrying light with a second detector (156), and determining in real-time at least one selected property of the blended materials based on the detector outputs.

30 Claims, 7 Drawing Sheets

U.S. PATENT DOCUMENTS

| | | | |
|---|---|---|---|
| 3,761,724 | A | 9/1973 | Dennis |
| 4,499,378 | A | 2/1985 | Miyatake et al. |
| 4,607,914 | A | 8/1986 | Fienup |
| 4,687,337 | A | 8/1987 | Stewart et al. |
| 4,704,536 | A | 11/1987 | Sugiyama et al. |
| 4,891,574 | A | 1/1990 | Nagaya et al. |
| 4,981,332 | A | 1/1991 | Smith |
| 5,071,526 | A | 12/1991 | Pletcher et al. |
| 5,090,807 | A | 2/1992 | Tai |
| 5,103,340 | A | 4/1992 | Dono et al. |
| 5,137,364 | A | 8/1992 | McCarthy |
| 5,150,236 | A | 9/1992 | Patel |
| 5,223,715 | A | 6/1993 | Taylor |
| 5,259,381 | A | 11/1993 | Cheung et al. |
| 5,406,082 | A | 4/1995 | Pearson et al. |
| 5,504,332 | A * | 4/1996 | Richmond et al. ........ 250/339.12 |
| 5,622,868 | A | 4/1997 | Clarke et al. |
| 5,641,962 | A | 6/1997 | Perry et al. |
| 5,710,655 | A | 1/1998 | Rumbaugh et al. |
| 5,734,098 | A | 3/1998 | Kraus et al. |
| 5,737,076 | A | 4/1998 | Glaus et al. |
| 5,760,399 | A | 6/1998 | Trygstad |
| 5,781,289 | A | 7/1998 | Sabsabi et al. |
| 5,799,231 | A | 8/1998 | Gates et al. |
| 5,831,742 | A | 11/1998 | Watson et al. |
| 5,905,571 | A | 5/1999 | Butler et al. |
| 5,939,717 | A | 8/1999 | Mullins |
| 5,941,821 | A | 8/1999 | Chou |
| 5,945,676 | A | 8/1999 | Khalil et al. |
| 5,946,088 | A * | 8/1999 | Aldridge ........................ 356/300 |
| 5,946,089 | A | 8/1999 | Duer |
| 5,991,048 | A | 11/1999 | Karlson et al. |
| 6,006,585 | A | 12/1999 | Forster |
| 6,040,914 | A | 3/2000 | Bortz et al. |
| 6,124,937 | A | 9/2000 | Mittenzwey et al. |
| 6,137,108 | A | 10/2000 | DeThomas et al. |
| 6,176,323 | B1 | 1/2001 | Weirich et al. |
| 6,198,531 | B1 | 3/2001 | Myrick et al. |
| 6,304,854 | B1 | 10/2001 | Harris |
| 6,317,648 | B1 | 11/2001 | Sleep et al. |
| 6,347,131 | B1 | 2/2002 | Gusterson |
| 6,350,389 | B1 | 2/2002 | Fujishima et al. |
| 6,420,708 | B2 | 7/2002 | Wilks, Jr. et al. |
| 6,430,513 | B1 | 8/2002 | Wang et al. |
| 6,437,326 | B1 | 8/2002 | Yamate et al. |
| 6,469,785 | B1 | 10/2002 | Duveneck et al. |
| 6,476,384 | B1 | 11/2002 | Mullins et al. |
| 6,490,035 | B1 * | 12/2002 | Folestad et al. ................ 356/319 |
| 6,517,230 | B1 * | 2/2003 | Afnan et al. .................. 366/142 |
| 6,522,945 | B2 | 2/2003 | Sleep et al. |
| 6,529,276 | B1 | 3/2003 | Myrick |
| 6,573,999 | B1 | 6/2003 | Yang |
| 6,600,560 | B2 | 7/2003 | Mikkelsen et al. |
| 6,630,663 | B2 | 10/2003 | Murphy et al. |
| 6,667,802 | B2 | 12/2003 | Faus et al. |
| 6,690,464 | B1 | 2/2004 | Lewis et al. |
| 6,697,195 | B2 | 2/2004 | Weber et al. |
| 6,707,043 | B2 | 3/2004 | Coates et al. |
| 6,711,503 | B2 | 3/2004 | Haaland |
| 6,737,654 | B2 | 5/2004 | Ducourant |
| 6,741,335 | B2 | 5/2004 | Kinrot et al. |
| 6,748,334 | B1 | 6/2004 | Perez et al. |
| 6,765,212 | B2 | 7/2004 | Goetz et al. |
| 6,771,369 | B2 | 8/2004 | Rzasa et al. |
| 6,776,517 | B2 * | 8/2004 | Afnan et al. .................. 366/142 |
| 6,798,518 | B2 | 9/2004 | Difoggio et al. |
| 6,853,447 | B2 | 2/2005 | Goetz |
| 6,870,629 | B1 | 3/2005 | Vogel et al. |
| 6,952,267 | B2 | 10/2005 | Rarac |
| 6,980,285 | B1 | 12/2005 | Hansen |
| 6,982,431 | B2 | 1/2006 | Modlin et al. |
| 6,995,840 | B2 | 2/2006 | Hagler |
| 7,006,214 | B2 | 2/2006 | Rzasa et al. |
| 7,123,844 | B2 | 10/2006 | Myrick |
| 7,138,156 | B1 | 11/2006 | Myrick et al. |
| 7,145,145 | B2 | 12/2006 | Benson |
| 7,173,239 | B2 | 2/2007 | DiFoggio |
| 7,245,374 | B2 | 7/2007 | Hendriks |
| 7,271,883 | B2 | 9/2007 | Newell et al. |
| 7,399,968 | B2 | 7/2008 | Lewis et al. |
| 7,405,825 | B2 | 7/2008 | Schuurmans et al. |
| 7,411,729 | B2 | 8/2008 | Lyama et al. |
| 7,569,354 | B2 | 8/2009 | Okano et al. |
| 7,623,233 | B2 | 11/2009 | Freese et al. |
| 7,652,767 | B2 | 1/2010 | Harsh et al. |
| 7,671,973 | B2 | 3/2010 | Van Beek et al. |
| 7,697,141 | B2 | 4/2010 | Jones et al. |
| 7,853,104 | B2 | 12/2010 | Oota et al. |
| 7,889,346 | B2 | 2/2011 | Myrick et al. |
| 7,899,636 | B2 * | 3/2011 | Bakker ........................ 702/85 |
| 7,911,605 | B2 | 3/2011 | Myrick et al. |
| 7,920,258 | B2 | 4/2011 | Myrick et al. |
| 2001/0034064 | A1 | 10/2001 | Turner et al. |
| 2002/0008215 | A1 | 1/2002 | Evans |
| 2002/0050567 | A1 | 5/2002 | Boudet et al. |
| 2002/0071118 | A1 | 6/2002 | Shinbori et al. |
| 2002/0108892 | A1 | 8/2002 | Goetz et al. |
| 2002/0109094 | A1 | 8/2002 | Goetz et al. |
| 2002/0154315 | A1 | 10/2002 | Myrick |
| 2003/0056581 | A1 | 3/2003 | Turner et al. |
| 2003/0059820 | A1 | 3/2003 | Vo-Dinh |
| 2003/0071988 | A1 | 4/2003 | Smith et al. |
| 2003/0094495 | A1 | 5/2003 | Knowles et al. |
| 2003/0111606 | A1 | 6/2003 | Berghmans et al. |
| 2003/0117628 | A1 | 6/2003 | Harju et al. |
| 2003/0202179 | A1 | 10/2003 | Larsen et al. |
| 2004/0012782 | A1 | 1/2004 | Mason et al. |
| 2004/0106098 | A1 | 6/2004 | Chen et al. |
| 2004/0160601 | A1 | 8/2004 | Womble et al. |
| 2004/0227086 | A1 | 11/2004 | Haug et al. |
| 2005/0032235 | A1 * | 2/2005 | Tummala et al. ............. 436/171 |
| 2005/0077476 | A1 | 4/2005 | Poteet et al. |
| 2005/0087132 | A1 | 4/2005 | Dickey et al. |
| 2005/0167264 | A1 | 8/2005 | Sternbergh et al. |
| 2005/0251289 | A1 | 11/2005 | Bonney et al. |
| 2005/0264815 | A1 | 12/2005 | Wechsler et al. |
| 2005/0288906 | A1 | 12/2005 | Drennen, III et al. |
| 2006/0051036 | A1 | 3/2006 | Treado et al. |
| 2006/0093523 | A1 | 5/2006 | Norman |
| 2006/0142955 | A1 | 6/2006 | Jones et al. |
| 2006/0153492 | A1 | 7/2006 | Treves et al. |
| 2006/0158734 | A1 | 7/2006 | Schuurmans et al. |
| 2006/0197015 | A1 | 9/2006 | Sterling et al. |
| 2006/0276697 | A1 | 12/2006 | Demuth et al. |
| 2007/0035737 | A1 | 2/2007 | Andrews et al. |
| 2007/0137292 | A1 | 6/2007 | Xian et al. |
| 2007/0201136 | A1 | 8/2007 | Myrick |
| 2007/0282647 | A1 | 12/2007 | Freese et al. |
| 2007/0291251 | A1 * | 12/2007 | Rensen et al. .................. 356/39 |
| 2007/0294094 | A1 | 12/2007 | Alessandrini et al. |
| 2008/0111064 | A1 | 5/2008 | Andrews et al. |
| 2008/0231849 | A1 | 9/2008 | Myrick |
| 2008/0276687 | A1 | 11/2008 | Myrick et al. |
| 2008/0309930 | A1 | 12/2008 | Rensen |
| 2009/0002697 | A1 | 1/2009 | Freese et al. |
| 2009/0015819 | A1 | 1/2009 | Van Beek et al. |
| 2009/0033933 | A1 | 2/2009 | Myrick |
| 2009/0073433 | A1 | 3/2009 | Myrick et al. |
| 2009/0097024 | A1 | 4/2009 | Blackburn et al. |
| 2009/0140144 | A1 | 6/2009 | Myrick et al. |
| 2009/0216504 | A1 | 8/2009 | Priore et al. |
| 2009/0219538 | A1 | 9/2009 | Myrick et al. |
| 2009/0250613 | A1 | 10/2009 | Myrick et al. |
| 2009/0299946 | A1 | 12/2009 | Myrick et al. |
| 2009/0316150 | A1 | 12/2009 | Myrick et al. |
| 2010/0042348 | A1 | 2/2010 | Bakker |
| 2010/0073666 | A1 | 3/2010 | Perkins et al. |
| 2010/0141952 | A1 | 6/2010 | Myrick et al. |
| 2010/0149537 | A1 | 6/2010 | Myrick et al. |
| 2010/0153048 | A1 | 6/2010 | Myrick et al. |
| 2010/0182600 | A1 | 7/2010 | Freese et al. |
| 2010/0195105 | A1 | 8/2010 | Myrick et al. |
| 2010/0211329 | A1 | 8/2010 | Farquharson et al. |
| 2010/0245096 | A1 | 9/2010 | Jones et al. |
| 2010/0265509 | A1 | 10/2010 | Jones et al. |

| | | | |
|---|---|---|---|
| 2010/0302539 | A1 | 12/2010 | Myrick et al. |
| 2010/0305741 | A1 | 12/2010 | Myrick |
| 2010/0328669 | A1 | 12/2010 | Myrick et al. |

FOREIGN PATENT DOCUMENTS

| | | |
|---|---|---|
| EP | 1969326 A1 | 9/2008 |
| EP | 1974201 A1 | 10/2008 |
| EP | 2087328 A2 | 8/2009 |
| EP | 2140238 A1 | 1/2010 |
| WO | 2004/057284 A1 | 7/2004 |
| WO | 2005/062006 A1 | 7/2005 |
| WO | 2005/062986 A2 | 7/2005 |
| WO | WO 2005062006 A1 * | 7/2005 |
| WO | 2006/031733 A2 | 3/2006 |
| WO | 2006/064446 A1 | 6/2006 |
| WO | 2006/137902 A2 | 12/2006 |
| WO | 2007/061435 A1 | 5/2007 |
| WO | 2007/061436 A1 | 5/2007 |
| WO | 2007/061437 A1 | 5/2007 |
| WO | 2007/062202 A1 | 5/2007 |
| WO | 2007/062224 A1 | 5/2007 |
| WO | 2007/064578 A2 | 6/2007 |
| WO | 2008/002903 A2 | 1/2008 |
| WO | 2008/057912 A2 | 5/2008 |
| WO | 2008/057913 A2 | 5/2008 |
| WO | 2008/121684 A1 | 10/2008 |

OTHER PUBLICATIONS

E.B. Martin et al., "Process Performance Monitoring Using Multivariate Statistical Process Control", IEE Proc.—Control Theory Appl., vol. 143, No. 2, pp. 132-144, Mar. 1996.
Mandelis et al., "Theory of Photopyroelectric Spectroscopy of Solids", Journal of Applied Physics, vol. 57, No. 9, pp. 4421-4430, 1985.
Zagonel et al., "Multivariate Monitoring of Soybean Oil Ethanolysis by FTIR", Talanta, vol. 63, No. 4, pp. 1021-1025, 2004.
Inon et al., "Combination of Mid- and Near-Infrared Spectroscopy for the Determination of the Quality Properties of Beers", Analytica Chimica Acta, vol. 571, No. 2, pp. 167-174, 2006.
Czarnik-Matusewicz et al., "Temperature-Dependent Water Structural Transitions Examined by Near-IR and Mid-IR Spectra Analyzed by Multivariate Curve Resolution and Two-Dimensional Correlation Spectroscopy", Analytica Chimica Acta, vol. 544, No. 1-2, pp. 15-25, 2005.
Pimentel et al., "Determination of Biodiesel Content when Blended with Mineral Diesel Fuel Using Infrared Spectroscopy and Multivariate Calibration", Microchemical Journal, vol. 82, No. 2, pp. 201-206, 2006.
Ghesti et al., "Application of Raman Spectroscopy to Monitor and Quantify Ethyl Esters in Soybean Oil Transesterification", Journal of the American Oil Chemists' Society, vol. 83, pp. 597-601, 2006.
Dereniak et al., *Infrared Detectors and Systems*, John Wiley & Sons: New York, Chapter 9, pp. 395-438, 1996.
Prystay et al., "Thermophysical Measurements and Interfacial Studies in Ultrathin Polymer Films Using Homodyne Photothermal Spectrometry", Applied Spectroscopy, vol. 47, No. 4, pp. 501-514, 1993.
Simcock et al., "Tuning D* with Modified Thermal Detectors", Applied Spectroscopy, vol. 60, No. 12, pp. 1469-1476, 2006.
Lang, "Ferroelectric Polymers and Ceramic-Polymer Composites", Key Engineering Materials, vol. 92-93, pp. 83-142. 1994.
Profeta et al., "Spectral Resolution in Multivariate Optical Computing", Spectrochimica Acta Part A: Molecular and Biomolecular Spectroscopy, vol. 67, pp. 483-502, 2007.
Power et al., "Rapid Recovery of Wide Bandwidth Photothermal Signals via Homodyne Photothermal Spectrometry: Theory and Methodology", Applied Spectroscopy, vol. 47, No. 4, pp. 489-500, 1993.
Workman, Handbook of Organic Compounds: NIR, IR, Raman and UV-Vis Spectra Featuring Polymers and Surfactants (a 3-volume set); Academic Press: San Diego, vol. 3, pp. 96-160, 2001.
Knothe, "Analyzing Biodiesel: Standards and Other Methods", Journal of the American Oil Chemists Society, vol. 83, No. 10, pp. 823-833, 2006.
E.D. Palik, *Handbook of Optical Constants of Solids I*, Academic Press, San Diego, pp. 350-357, 1998.

M.L. Myrick, "Multivariate optical elements simplify spectroscopy", Laser Focus World 38, 91-94, 2002.
O. Soyemi et al.,"Design and testing of a multivariate optical element: The first demonstration of multivariate optical computing for predictive spectroscopy", Anal. Chem. 73, No. 6, pp. 1069-1079, (2001).
M.L. Myrick et al., "A single-element all-optical approach to chemometric prediction", Vib. Sepctrosc. 28, 73-81, 2002.
A.M.C. Prakash et al., "Optical regression: a method for improving quantitative precision of multivariate prediction with single channel spectrometers", Chemom. Intell. Lab. Syst. 46, 265-274, 1999.
R.A. Deverse et al., "Realization of the Hadamard multiplex advantage using a programmable optical mask in a dispersive flat-field near-infrared spectrometer", Appl. Spectrosc. 54, 1751-1758, 2000.
F.G. Haibach et al., "Precision in multivariate optical computing", Appl. Optics 43, 2130-2140, 2004.
M.L. Myrick et al., "Application of multivariate optical computing to simple near-infrared point measurements", Proceedings of the SPIE, Bellingham, VA, US, vol. 4574, pp. 208-215, 2002.
O.S. Heavens, *Optical Properties of Thin Solid Films*, Dover Publications, Inc., Mineola, USA, pp. 62-81, 242-249, 1991.
S. Betancourt et al., "Analyzing Hydrocarbons in the Borehole", Oilfield Review, pp. 54-61, Autumn 2003.
D. Eastwood et al., "Field applications pf stand-off sensing using visible/NIR multivariate optical computing", Ground and Air Pollution Monitoring and Remediation, SPIE vol. 4199, pp. 105-114, 2001.
Haibach et al., "On-line Reoptimization of Filter Designs for Multivariate Optical Elements", Applied Optics, vol. 42, No. 10, pp. 1833-1836, Apr. 1, 2003.
Mullins et al., "Gas-Oil Ratio of Live Crude Oils Determined by Near-Infrared Spectroscopy", Optical Methods for Industrial Processes, Proceedings of SPIE vol. 4201, pp. 73-81, 2001.
M.P. Nelson et al., "Multivariate optical computation for predictive spectroscopy", SPIE Vo. 3261, pp. 232-243, 1998.
O. Soyemi et al., "A Simple Optical Computing Device For Chemical Analysis", Proceedings of SPIE Vo. 4284, pp. 17-28, 2001.
O. Soyemi et al., "Design of angle tolerant multivariate optical elements for chemical imaging", Applied Optics, vol. 41, No. 10, pp. 1936-1941, Apr. 1, 2002.
O. Soyemi et al., "Nonlinear Optimization Algorithm for Multivariate Optical Element Design", Applied Spectroscopy, vol. 56, No. 4, pp. 477-487, 2002.
O. Soyemi et al., "Novel Filter Design Algorithm for Multivariate Optical Computing", Advanced Environmental and Chemical Sensing Technology, Proceedings of SPIE Vo. 4205, pp. 288-299, 2001.
Strausz et al., "About the Colloidal Nature of Asphaltenes and the MW of Covalent Monomeric Units", American Chemical Society, Energy and Fuels 16, No. 4. pp. 809-822, 2002 (abstract).
N. Aske et al., "Determination of Saturate, Aromatic, Resin. and Asphitenic (SARA) Components in Crude Oils by Means of Infrared and Near-Infrared Spectroscopy", American Chemical Society, Energy and Fuels 15, No. 5, pp. 1304-1312, 2001.
N. Aske et al., "Asphallene Aggregation from Crude Oils and Models Systems Studied by High-Pressure NIR Spectroscopy", Energy and Fuels, American Chemical Society, 16, No. 5, pp. 1287-1295, 2002.
Sastry et al., "Determination of Physiocochemical Properties and Carbon-Type Analysis of Base Oils Using Mid-IR Spectroscopy and Partial Least Squares Regression Analysis", American Chemical Society, Energy and Fuels 12, No. 2, pp. 304-311, 1998.
Y. Yan et al., "Flourscence Fingerprint of Waters: Excitation-Emission Matrix Spectroscopy as a Tracking Tool", Applied Spectroscopy, vol. 54, No. 10, pp. 1539-1542, 2000.
M.P. Nelson et al., "Multivariate optical computation for predictive spectroscopy", Analytical Chemistry, vol. 70, No. 1, pp. 73-82, Jan. 1, 1998.
M.P. Nelson et al., "Fabrication and evalution of a dimension-reduction fiberoptic system for chemical imaging applications", Review of Scientific Instruments, vol. 70, No. 6, pp. 2836-2843, Jun. 1999.
M.L. Myrick, "New approaches to implementing predictive spectroscopy", Proceedings of the SPIE Conference on Pattern Recognition, Chemomatrics, and Imaging for Optical Environmental Monitoring, SPIE vol. 3854, pp. 96-102, Sep. 1999.

M. Groner et al., "Identification of Major Water-Soluble Fluorescent Components of Some Petrochemicals", Marine Pollution Bulletin, vol. 42, No. 10, pp. 935-941, 2001.

M.V. Schiza et al., "Use of a 2D to 1D Dimension Reduction Fiber-Optic Array for Multiwavelength Imaging Sensors", Applied Spectroscopy, vol. 55, No. 2, pp. 217-226, 2001.

M. L. Myrick et al., "Spectral tolerance determination for miltivariate optical element design", Fresenius J Anal Chem, 369:351-355, 2001.

R.J. Priore et al., "Miniature Stereo Spectral Imaging System for Multivariate Optical Computing", Applied Spectroscopy, vol. 58, No. 7, pp. 870-873, 2004.

M.L. Myrick et al., "Use of Molecular Symmetry To Describe Pauli Principle Effects on the Vibration-Rotation Spectroscopy of $CO_2(g)$", Journal of Chemical Education, vol. 81, No. 3, pp. 379-382, Mar. 2004.

M.N. Simcock et al., "Precision in imaging multivariate optical computing", Applied Optics, vol. 46., No. 7, pp. 1066-1080, Mar. 1, 2007.

Ozturk et al., "Filtering Characteristics of Hybrid Integrated Polymer and Compound Semiconductor Waveguides", In: Journal of Lightwave Technology, vol. 20, No. 8, pp. 1530-1536, Aug. 2002.

P.G. Miney et al., "A New Optically Reflective Thin Layer Electrode (ORTLE) Window: Gold on a Thin Porous Alumina Film Used to Observe the Onset of Water Reduction", Electroanalysis, 16, No. 1-2, pp. 113-119, 2004.

Mullins et al., "Gas-Oil Ratio of Live Crude Oils Determined by Near-Infrared Spectroscopy", Applied Spectroscopy, vol. 55, No. 2, pp. 197-201, 2001.

\* cited by examiner

OPTICAL ANALYSIS SYSTEM FOR DYNAMIC REAL-TIME DETECTION AND MEASUREMENT

CROSS-REFERENCE TO RELATED APPLICATIONS

This application claims benefit of U.S. Provisional Patent Application Ser. No. 60/740,054, filed Nov. 28, 2005 and U.S. Provisional Patent Application Ser. No. 60/773,276 filed Feb. 14, 2006.

FIELD OF THE INVENTION

The present invention relates to improvements related to system design, fabrication and operation of multivariate optical elements. More particularly, the invention relates to methodologies of using multivariate optical computing systems to illuminate a sample in which information about the sample can be analyzed from the reflected or transmitted light in real time or near real time.

BACKGROUND OF THE INVENTION

Light conveys information through data. When light interacts with matter, for example, it carries away information about the physical and chemical properties of the matter. A property of the light, for example, its intensity, may be measured and interpreted to provide information about the matter with which it interacted. That is, the data carried by the light through its intensity may be measured to derive information about the matter. Similarly, in optical communications systems, light data is manipulated to convey information over an optical transmission medium, for example fiber optic cable. The data is measured when the light signal is received to derive information.

In general, a simple measurement of light intensity is difficult to convert to information because it likely contains interfering data. That is, several factors may contribute to the intensity of light, even in a relatively restricted wavelength range. It is often impossible to adequately measure the data relating to one of these factors since the contribution of the other factors is unknown.

It is possible, however, to derive information from light. An estimate may be obtained, for example, by separating light from several samples into wavelength bands and performing a multiple linear regression of the intensity of these bands against the results of conventional measurements of the desired information for each sample. For example, a polymer sample may be illuminated so that light from the polymer carries information such as the sample's ethylene content. Light from each of several samples may be directed to a series of bandpass filters which separate predetermined wavelength bands from the light. Light detectors following the bandpass filters measure the intensity of each light band. If the ethylene content of each polymer sample is measured using conventional means, a multiple linear regression of ten measured bandpass intensities against the measured ethylene content for each sample may produce an equation such as:

$$y = a_0 + a_1 w_1 + a_2 w_2 + \ldots + a_{10} w_{10} \quad \text{(``Equation 1'')}$$

where y is ethylene content, $a_n$ are constants determined by the regression analysis, and $w_n$ is light intensity for each wavelength band.

Equation 1 may be used to estimate ethylene content of subsequent samples of the same polymer type. Depending on the circumstances, however, the estimate may be unacceptably inaccurate since factors other than ethylene may affect the intensity of the wavelength bands. These other factors may not change from one sample to the next in a manner consistent with ethylene.

A more accurate estimate may be obtained by compressing the data carried by the light into principal components. To obtain the principal components, spectroscopic data is collected for a variety of samples of the same type of light, for example from illuminated samples of the same type of polymer. For example, the light samples may be spread into their wavelength spectra by a spectrograph so that the magnitude of each light sample at each wavelength may be measured. This data is then pooled and subjected to a linear-algebraic process known as singular value decomposition (SVD). SVD is at the heart of principal component analysis, which should be well understood in this art. Briefly, principal component analysis is a dimension reduction technique, which takes m spectra with n independent variables and constructs a new set of eigenvectors that are linear combinations of the original variables. The eigenvectors may be considered a new set of plotting axes. The primary axis, termed the first principal component, is the vector, which describes most of the data variability. Subsequent principal components describe successively less sample variability, until only noise is described by the higher order principal components.

Typically, the principal components are determined as normalized vectors. Thus, each component of a light sample may be expressed as $x_n z_n$, where $x_n$ is a scalar multiplier and $z_n$ is the normalized component vector for the $n_{th}$ component. That is, $z_n$ is a vector in a multi-dimensional space where each wavelength is a dimension. As should be well understood, normalization determines values for a component at each wavelength so that the component maintains it shape and so that the length of the principal component vector is equal to one. Thus, each normalized component vector has a shape and a magnitude so that the components may be used as the basic building blocks of all light samples having those principal components. Accordingly, each light sample may be described in the following format by the combination of the normalized principal components multiplied by the appropriate scalar multipliers:

$$x_1 z_1 + x_2 z_2 + \ldots + x_n z_n.$$

The scalar multipliers $x_n$ may be considered the "magnitudes" of the principal components in a given light sample when the principal components are understood to have a standardized magnitude as provided by normalization.

Because the principal components are orthogonal, they may be used in a relatively straightforward mathematical procedure to decompose a light sample into the component magnitudes, which accurately describe the data in the original sample. Since the original light sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Because the principal components are orthogonal, or perpendicular, to each other, the dot, or direct, product of any principal component with any other principal component is zero. Physically, this means that the components do not interfere with each other. If data is altered to change the magnitude of one component in the original light signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the light samples. Thus, in a mathematical sense, the principal components are components of the original light that do not interfere with each other and that represent the most compact description of the entire data carried by the light. Physically, each principal component is a light signal that forms a part of the original light signal. Each has a shape over some wavelength range within the original wavelength range. Summing the principal components produces the original signal, provided each component has the proper magnitude.

The principal components comprise a compression of the data carried by the total light signal. In a physical sense, the shape and wavelength range of the principal components describe what data is in the total light signal while the magnitude of each component describes how much of that data is there. If several light samples contain the same types of data, but in differing amounts, then a single set of principal components may be used to exactly describe (except for noise) each light sample by applying appropriate magnitudes to the components.

The principal components may be used to accurately estimate information carried by the light. For example, suppose samples of a certain brand of gasoline, when illuminated, produce light having the same principal components. Spreading each light sample with a spectrograph may produce wavelength spectra having shapes that vary from one gasoline sample to another. The differences may be due to any of several factors, for example differences in octane rating or lead content.

The differences in the sample spectra may be described as differences in the magnitudes of the principal components. For example, the gasoline samples might have four principal components. The magnitudes $x_n$ of these components in one sample might be J, K, L, and M, whereas in the next sample the magnitudes may be 0.94 J, 1.07K, 1.13 L and 0.86M. As noted above, once the principal components are determined, these magnitudes exactly describe their respective light samples.

Refineries desiring to periodically measure octane rating in their product may derive the octane information from the component magnitudes. Octane rating may be dependent upon data in more than one of the components. Octane rating may also be determined through conventional chemical analysis. Thus, if the component magnitudes and octane rating for each of several gasoline samples are measured, a multiple linear regression analysis may be performed for the component magnitudes against octane rating to provide an equation such as:

$$y = a_0 + a_1 x_1 + a_2 x_2 + a_3 x_3 + a_4 x_4 \quad \text{(``Equation 2'')}$$

where y is octane rating, $a_n$ are constants determined by the regression analysis, and $x_1$, $x_2$, $x_3$ and $x_4$ are the first, second, third and fourth principal component magnitudes, respectively.

Using Equation 2, which may be referred to as a regression vector, refineries may accurately estimate octane rating of subsequent gasoline samples. Conventional systems perform regression vector calculations by computer, based on spectrograph measurements of the light sample by wavelength. The spectrograph system spreads the light sample into its spectrum and measures the intensity of the light at each wavelength over the spectrum wavelength range. If the regression vector in the Equation 2 form is used, the computer reads the intensity data and decomposes the light sample into the principal component magnitudes $x_n$ by determining the dot product of the total signal with each component. The component magnitudes are then applied to the regression equation to determine octane rating.

To simplify the procedure, however, the regression vector is typically converted to a form that is a function of wavelength so that only one dot product is performed. Each normalized principal component vector $z_n$ has a value over all or part of the total wavelength range. If each wavelength value of each component vector is multiplied by the regression constant $a_n$ corresponding to the component vector, and if the resulting weighted principal components are summed by wavelength, the regression vector takes the following form:

$$y = a_0 + b_1 u_1 + b_2 u_2 + \ldots + b_n u_n \quad \text{(``Equation 3'')}$$

where y is octane rating, $a_0$ is the first regression constant from Equation 2, $b_n$ is the sum of the multiple of each regression constant $a_n$ from Equation 2 and the value of its respective normalized regression vector at wavelength n, and $u_n$ is the intensity of the light sample at wavelength n. Thus, the new constants define a vector in wavelength space that directly describes octane rating. The regression vector in a form as in Equation 3 represents the dot product of a light sample with this vector.

Normalization of the principal components provides the components with an arbitrary value for use during the regression analysis. Accordingly, it is very unlikely that the dot product result produced by the regression vector will be equal to the actual octane rating. The number will, however, be proportional to the octane rating. The proportionality factor may be determined by measuring octane rating of one or more samples by conventional means and comparing the result to the number produced by the regression vector. Thereafter, the computer can simply scale the dot product of the regression vector and spectrum to produce a number approximately equal to the octane rating.

In a conventional spectroscopy analysis system, a laser directs light to a sample by a bandpass filter, a beam splitter, a lens and a fiber optic cable. Light is reflected back through the cable and the beam splitter to another lens to a spectrograph. The spectrograph separates light from the illuminated sample by wavelength so that a detection device such as a charge couple detector can measure the intensity of the light at each wavelength. The charge couple detector is controlled by controller and cooled by a cooler. The detection device measures the light intensity of light from the spectrograph at each wavelength and outputs this data digitally to a computer, which stores the light intensity over the wavelength range. The computer also stores a previously derived regression vector for the desired sample property, for example octane, and sums the multiple of the light intensity and the regression vector intensity at each wavelength over the sampled wavelength range, thereby obtaining the dot product of the light from the substance and the regression vector. Since this number is proportional to octane rating, the octane rating of the sample is identified.

Since the spectrograph separates the sample light into its wavelengths, a detector is needed that can detect and distinguish the relatively small amounts of light at each wavelength. Charge couple devices provide high sensitivity throughout the visible spectral region and into the near infrared with extremely low noise. These devices also provide high quantum efficiency, long lifetime, imaging capability and solid-state characteristics. Unfortunately, however, charge couple devices and their required operational instrumentation are very expensive. Furthermore, the devices are sensitive to environmental conditions. In a refinery, for example, they must be protected from explosion, vibration and temperature fluctuations and are often placed in protective housings approximately the size of a refrigerator. The power requirements, cooling requirements, cost, complexity and maintenance requirements of these systems have made them impractical in many applications.

Multivariate optical computing (MOC) is a powerful predictive spectroscopic technique that incorporates a multi-wavelength spectral weighting directly into analytical instrumentation. This is in contrast to traditional data collection routines where digitized spectral data is post processed with a computer to correlate spectral signal with analyte concentration. Previous work has focused on performing such spectral weightings by employing interference filters called Multivariate Optical Elements (MOEs). Other researchers have realized comparable results by controlling the staring or integration time for each wavelength during the data collection process. All-optical computing methods have been shown to produce similar multivariate calibration models, but the measurement precision via an optical computation is superior to a traditional digital regression.

MOC has been demonstrated to simplify the instrumentation and data analysis requirements of a traditional multivariate calibration. Specifically, the MOE utilizes a thin film interference filter to sense the magnitude of a spectral pattern. A no-moving parts spectrometer highly selective to a particular analyte may be constructed by designing simple calculations based on the filter transmission and reflection spectra. Other research groups have also performed optical computations through the use of weighted integration intervals and acousto-optical tunable filters digital mirror arrays and holographic gratings.

The measurement precision of digital regression has been compared to various optical computing techniques including MOEs, positive/negative interference filters and weighted-integration scanning optical computing. In a high signal condition where the noise of the instrument is limited by photon counting, optical computing offers a higher measurement precision when compared to its digital regression counterpart. The enhancement in measurement precision for scanning instruments is related to the fraction of the total experiment time spent on the most important wavelengths. While the detector integrates or coadds measurements at these important wavelengths, the signal increases linearly while the noise increases as a square root of the signal. Another contribution to this measurement precision enhancement is a combination of the Felgott's and Jacquinot's advantage, which is possessed by MOE optical computing.

While various methodologies have been developed to enhance measurement accuracy in Optical Analysis Systems, the industry requires a system in which the spectral range of the illumination source can be controlled; in which light can be shined directly onto a sample with or without fiber optic probes; and in which the reflected or transmitted light can be analyzed in real time or near real time

SUMMARY OF THE INVENTION

In an aspect of the invention, a method of real-time processing and monitoring includes blending a material of interest with a secondary material; illuminating the blended materials with a light; reflecting light carrying information about the blended materials through at least one multivariate optical element to produce a first signal; detecting the first signal at a first detector; detecting a deflected portion of the light at a second detector; and determining, in real time, at least one selected property of at least one of the blended materials as the material of interest and the secondary material are blended based upon respective detector outputs. According to this aspect of the invention, real time is faster than about 30 seconds, more preferably faster than about 5 seconds, still more preferably faster than about 1 second, further preferably faster than about $1/10$ of a second, still further preferably faster than about $1/100$ of a second, and most preferably faster than about $1/1000$ of a second.

In another aspect of the invention, a method of real-time pharmaceutical processing and monitoring can include moving a plurality of portions of pharmaceutical product past an inspection point, illuminating at least one portion of the pharmaceutical product with a spectral-specific light though an optic window, the window configured to focus the spectral-specific light onto a portion at the inspection point, reflecting light carrying information about the portion through at least one multivariate optical element to produce a first signal, detecting the first signal at a first detector, detecting a deflected portion of the spectral-specific light at a second detector, and determining, in real time, at least one selected property of the portion as it moves past the inspection point based upon the detector outputs.

The portions can comprise pharmaceutical tablets, trays or other containers of powders, or partially- or fully-enclosed sample containers at least partially transparent to light focused onto the portion. The portions can move past the inspection point at a rate between about 1 portion/second and about 5 portions/second, with the monitoring occurring in real-time at high speeds.

Other aspects and advantages of the invention are described in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

DETAILED DESCRIPTION OF THE DISCLOSURE

Figure 1:
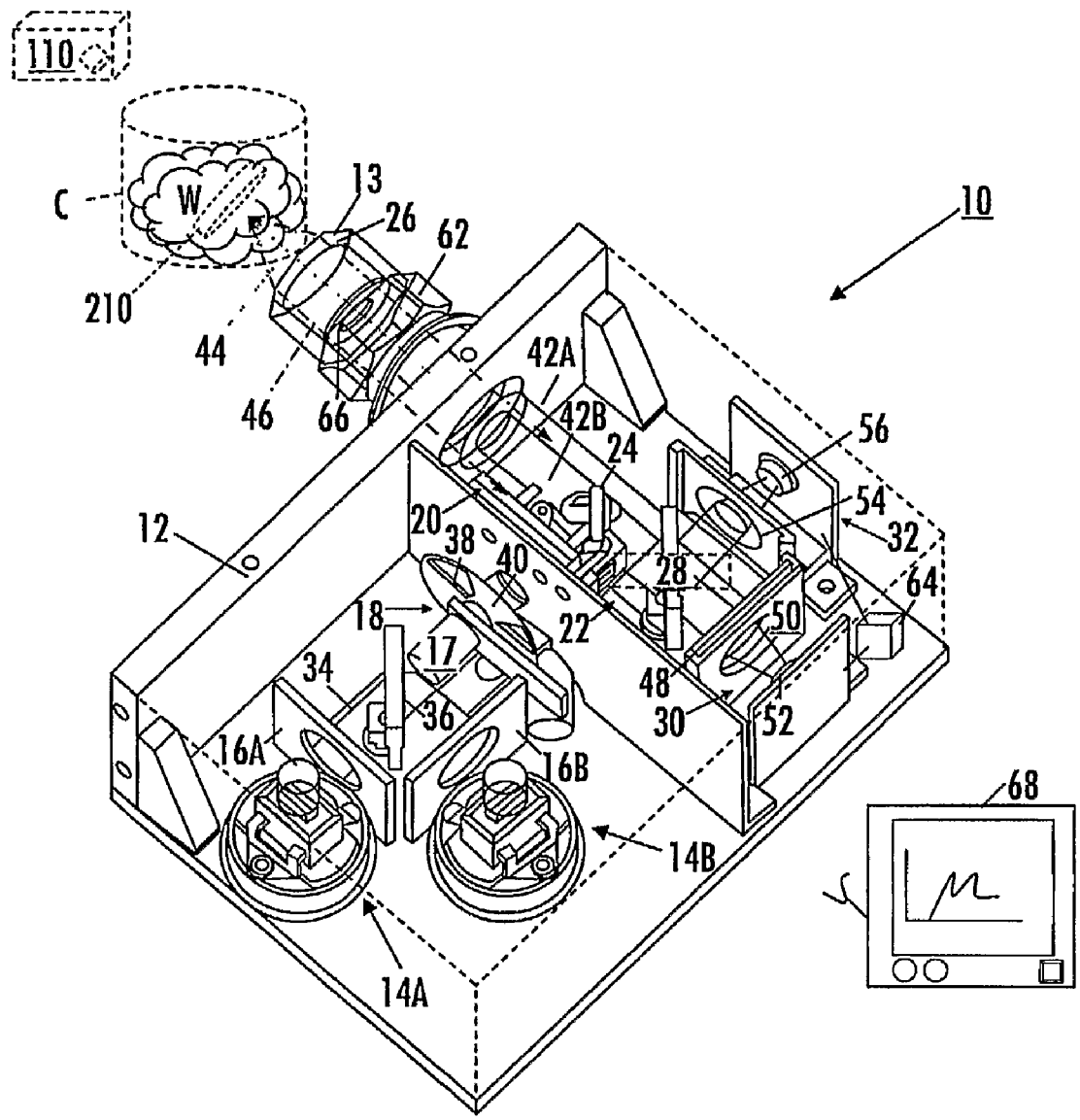
FIG. 1 is a top perspective view of one embodiment of a real time measurement system according to an aspect of the present invention.

Detailed reference will now be made to the drawings in which examples embodying the present invention are shown. The detailed description uses numerical and letter designations to refer to features of the drawings. Like or similar designations of the drawings and description have been used to refer to like or similar parts of the invention.

The drawings and detailed description provide a full and written description of the invention, and of the manner and process of making and using it, so as to enable one skilled in the pertinent art to make and use it, as well as the best mode of carrying out the invention. However, the examples set forth in the drawings and detailed description are provided by way of explanation only and are not meant as limitations of the invention. The present invention thus includes any modifications and variations of the following examples as come within the scope of the appended claims and their equivalents.

Figure 2:
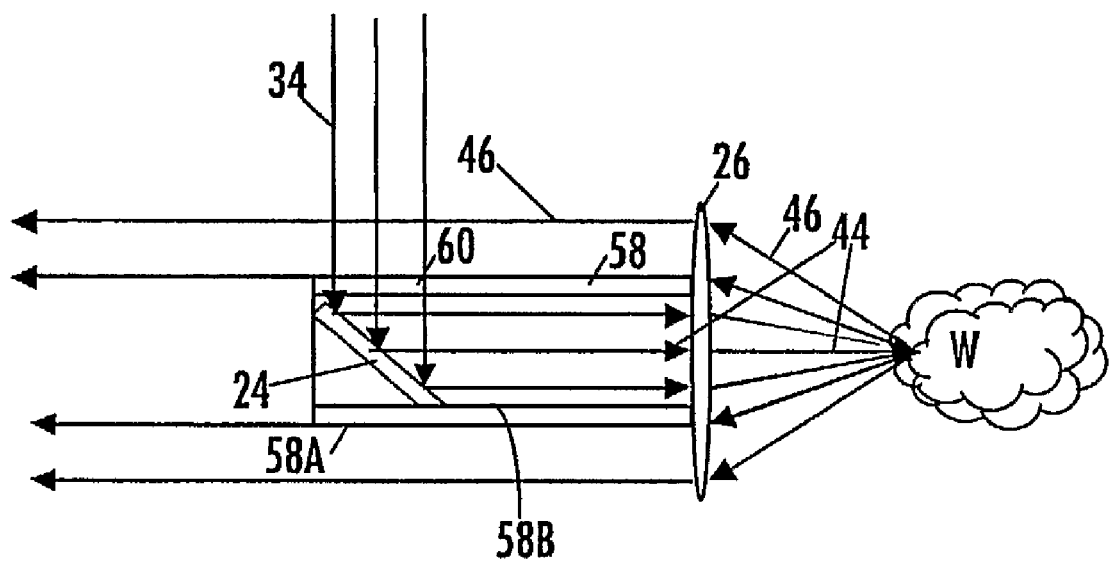
FIG. 2 is a schematic view of a concentric cavity as in FIG. 1 in accordance with a further aspect of the present invention.

As generally shown in FIGS. 1 and 2, an optical analysis system according to an aspect of the invention is designated by the element number 10. The system 10 is designed around at least one application specific multivariate optical element (MOE) based on spectra typically provided by an end-user. System design takes into account representative spectra of compounds of interest, basic and expected concentrations of interest across a range of expected interferents. Also, the system 10 incorporates the desired spectral regions (UV, VIS, NIR, MIR, IR) of interest.

In the embodiment shown in FIG. 1, the optical analysis system 10 broadly includes a housing 12, a plurality of illumination or light sources 14A, 14B, a concentric light tube or cavity 22, a focusing lens 26, at least one beam splitter 28, a first detector 30 including a multivariate optical element 48 and a second detector 32. Although FIG. 1 shows a generally square- or rectangle-shaped, metallic housing 12 and two detectors 30, 32 arranged therein, the skilled artisan will instantly appreciate that a variety of shapes, dimensions, component placements and material makeup of the components can be substituted for the examples shown according to various requirements such as government regulations, customer specifications and the like.

As used herein, the term "light" is broadly used to mean any form of radiation or radiative energy including, for instance, visible light or light in the infrared region. "Light" is also referred to herein as a light signal, a light beam, a light ray and the like to mean any form of radiative energy in the electromagnetic spectrum. Similarly, the term "transmission" can mean transmission of radiative energy onto a surface of a sample; penetration, however slight, into a sample such as a particulate sample or opaque fluid sample; or passage through a sample such as a fluid sample.

Moreover, as discussed below with respect to another embodiment of the invention, a workpiece or sample W can be analyzed using a PCR-type model without the beamsplitter 28 in an off-line approach. As used herein, the workpiece or sample W can mean an analyte undergoing analysis over a range of conditions. The sample can be a solid or a fluid including but not limited to a powder, a pharmaceutical powder mixed with lactose and other excipient materials, a chemical, a polymer, a petroleum product, a solution, a dispersion, an emulsion and combinations of these solids and fluids.

The skilled artisan will also understand that although the system can be a measurement system operating in reflectance mode, the system can also be configured to operate in a transmission mode in which light is shone through the sample W from an incident side of the sample W to a similar detection system 110 on another side of the sample W. Alternatively, or additionally, a mirrored surface 210 can be placed within the transmissive sample to reflect the light back into the detection system 10. Therefore, the invention is not limited only to the examples shown in the figures.

With more particular reference to FIG. 1, the housing 12 (shown partially in phantom for clarity) can be metal such as stainless steel, a plastic material such as high-density polyethylene (HDPE) or any durable material for protecting the components of the optical analysis system 10. As shown, sampling of the sample W is accomplished through a window 13 in the enclosed optical analysis system 10. Accordingly, the enclosed optical analysis system 10 can be used in a dangerous (e.g., explosive) environment. As will be described in detail below, the window 13 is transmissive in a known manner in a spectral region of interest.

As briefly introduced above, the illumination sources 14A, 14B are chosen to provide a source light 34, which has a spectral range determined by a spectral range of interest for the intended sample measurement. The illumination sources 14A, 14B are also chosen based on reliability, intensity, temperature generation, and other factors. The illumination sources 14A, 14B are also redundant to further enhance reliability. As shown in FIG. 1, the redundant illumination sources 14A, 14B can be oriented at 90 degrees from each other with a "50-50" beam splitter 36 located near their center point to provide a constant source of illumination.

FIG. 1 further shows a plurality of lenses 16A, 16B, respectively associated with each of the illumination sources 14A, 14B. The lenses 16A, 16B are used to collect the light signal 34 from the illumination sources 14A, 14B and to focus the light signal 34 on a modulator or chopper wheel 18, described below. As shown, the lenses 16A, 16B are positioned to capture as much of the light signal 34 as possible from the illumination sources 14A, 14B. Additionally, a chopper-focusing lens 17 is used to focus as much of the light signal 34 as possible through the chopper wheel 18. The skilled artisan will instantly recognize the lenses 16A, 16B, 17 are selected for focal length, position, material of construction and the like to enhance transmission (reduce loss) of the light signal 34. For example, in the design of the optical path, if the illumination sources 14A, 14B is a lamp, slight magnification or demagnification of the source is generally obtained at the sample W, depending on the ratios of the focal length, e.g., of the lens 16A to that placed after the illumination source 14A to collimate it. Ultimately, the image of the illumination source 14A on the sample W is directed toward the detectors 30, 32 as described below and again with some slight magnification or demagnification, depending on the ratios of the focal length, e.g., of the lenses 16A to that of, e.g., a lens 50 placed before the detector 30 to focus a reflected light 46 onto the detector 30. Thus, it should be understood that there is a relationship between the focal lengths of the lenses 16A, 16B that must be maintained in order to make sure the ultimate image of the source-excited region of the sample W that is formed on the detectors 30,32 is suited to the physical dimensions of the detectors 30,32.

The skilled artisan will further appreciate that the lenses 16A, 16B shown for example in FIG. 1 are plastic, Fresnel lenses well suited for use in an infrared (IR) region of about 1000 nanometers (nm) to about 3000 nm. However, the skilled artisan will understand that the lenses 16A, 16B are not limited to only plastic, Fresnel lenses and that other types of lenses and materials such as glass can be used for these lenses.

As further shown in FIG. 1, the chopper wheel 18 includes a plurality of alternating windows 38 and a plurality of alternating spokes 40. The alternating windows 38 and spokes 40 modulate the light signal 34 from about 50 Hertz (Hz) to about 5000 Hz to enable a plurality of photodetectors 52, 56 in the optical system 10 to perform properly, as will be further described below. As shown in this example, the chopper wheel 18 is a 10-window chopper wheel rotating at 40 Hz, which provides a chopped signal of 400 Hz. The number and arrangement of the windows 38 and spokes 40 and thus, the chopper frequency, are chosen based on several variables, including a rate of motion of the sample material W moving past the sampling window 13; a performance characteristic of the photodetectors 52,56 and amplification system; a predetermined sampling rate of the data collection and analysis system 10; physical properties of a chopper motor (not shown), control system (not shown), and the chopper wheel 18 (including material(s) of the windows 38).

More particularly, the number of windows 38 in the chopper wheel 18 can be adjusted to provide a suitable degree of signal modulation. In one aspect of the invention, the chopper wheel 18 has open windows 38 and black spokes 40, which block the light signal 34. In another aspect, different materials can be placed in the windows 38 to provide different spectral characteristics for the various windows 38. Moreover, the transmission characteristic of these windows 38 could be used as further spectral elements. The windows 38 can also contain multivariate optical elements (MOE) such as those described below with respect to a MOE 48 of the MOE detector 30.

FIG. 1 also shows a plurality of bandpass filters or spectral elements 20 located in a path of the light signal 34 after the light signal 34 has passed through the chopper wheel 18. As briefly discussed above, the spectral elements 20 are selected based on a desired application; i.e., to analyze a particular sample W. The spectral elements 20 are chosen so that the spectral region of illumination covers the desired range; i.e., related to a particular chemical material of interest. For example, if 1500-2000 nanometers (nm) of light wavelengths is the desired spectral region, the spectral elements 20 are selected to filter out wavelengths are not in that region. An example of these spectral elements is a SCHOTT brand filter, which can be a long pass, short pass, or band pass filter. By way of further example but not of limitation, some suitable materials for use as the spectral elements 20 are listed in the following table.

TABLE 1

Properties of Select Transmitting Materials

| Material | Comments | SWL cm-1 | LWL cm-1 | RI | Solubility g/100 g | Hardness Kg/mm 2 | MP °C. | pH Range |
|---|---|---|---|---|---|---|---|---|
| AMTIR | SeAsGe glass | 11000 | 593 | 2.5 | 0 | 170 | 370 | 1-9 |
| BaF 2 | Barium Fluoride | 66600 | 691 | 1.45 | 0.17 | 82 | 1280 | 5-8 |
| Ca F 2 | Calcium Fluoride | 79500 | 896 | 1.4 | 0.0017 | 158 | 1360 | 5-8 |
| CsI | Cesium Iodide, very hygroscopic | 42000 | 172 | 1.73 | 44 | 20 | 621 | NA |
| Diamond | Type IIa, strong IR absorbance between 2700-1800 cm-1 | 30000 | <2 | 2.4 | 0 | 5700 | 550 fp | 1-14 |
| Ge | Germanium, brittle, becomes opaque at elevated temperatures | 5500 | 432 | 4 | 0 | 780 | 936 | 1-14 |
| KBr | Potassium Bromide, most widely used for mid-IR applications | 48800 | 345 | 1.52 | 53 | 6 | 730 | NA |
| KCl | Potassium Chloride | 55600 | 385 | 1.45 | 35 | 7 | 776 | NA |
| KRS-5 | Thallium Bromide/ Thallium Iodide | 17900 | 204 | 2.37 | 0.05 | 40 | 414 | 5-8 |
| NaCl | Sodium Chloride | 52600 | 457 | 1.49 | 36 | 18 | 801 | NA |
| Polyethylene | For Far-IR, swells with some organic solvents | 625 | <4 | 1.52 | 0 | | 110 | 1.5-14 |
| SiO 2 | Silicon Dioxide | 50000 | 2315 | 1.53 | 0 | 460 | 1713 | 1-14 |

TABLE 1-continued

Properties of Select Transmitting Materials

| Material | Comments | SWL cm-1 | LWL cm-1 | RI | Solubility g/100 g | Hardness Kg/mm 2 | MP ° C. | pH Range |
|---|---|---|---|---|---|---|---|---|
| Si | Silicon, strong IR absorbance between 624-590 cm-1 | 8900 | 624.30 | 3.41 | 0 | 1150 | 1420 | 1-12 |
| ZnS | Zinc Sulfide | 17000 | 690 | 2.2 | 0 | 240 | 1830 | 5-9 |
| ZnSe | Zinc Selenide | 15000 | 461 | 2.4 | 0 | 120 | 1526 | 5-9 |

Note:
To convert from wavenumber (cm-1) to wavelength (μm), divide 10,000 by the wavenumber; e.g., 5500 cm-1 is equivalent to 1.8 μm or 1800 nm.
SWL—Shortest wavelength for transmission, 1 mm, 50% transmission
LWL—Longest wavelength for transmission, 1 mm, 50% transmission
RI—Refractive Index, at relevant wavelength
MP—Melting point
pH—negative log of hydrogen ion concentration With reference now to FIGS. 1 and 2, the light signal 34 exits the spectral elements 20 and reflects off a first mirror or turning mirror 24. It will be appreciated that although the turning mirror 24 is shown at an angle of about 45 degrees with the light signal 34 reflecting at this angle, the turning mirror 24 can be turned to any desired angle. As known to those skilled in the art, the turning mirror 24 can be a powered turning mirror powered by a battery, by electricity or the like. Further description of power sources and implementation with the turning mirror 24 is not necessary for one skilled in the art to understand this aspect of the invention. The skilled artisan will further appreciate that although the turning mirror 24 is shown as a unitary mirror, the invention can utilize multiple mirrors arranged in or adjustable to a variety of positions.

As further shown in FIGS. 1 and 2, the filtered and reflected light signal 34 becomes a reflected light 44 after being reflected by the turning mirror 24. The reflected light 44 thus continues down the concentric sampling tube 22, briefly introduced above, in a direction of the sample W. As shown and further described below, the concentric tube 22 includes an inner annular region (also referred to as tube or chamber) 42A and an outer annular region 42B (also, tube or chamber). In this example, the reflected light 44 is reflected along the inner annular region 42A. It will be understood that the illumination sources 14A, 14B and the detectors 30, 32 are shown in an exemplary orientation and can be reversed. It will be further appreciated that the light signal 34 and the reflected light 44 are shown collimated for simplicity. However, the light signal 34 and the reflected light 44 may not be completely collimated because the illumination sources 14A, 14B can be extended rather than point sources.

The focusing lens 26 in FIGS. 1 and 2 is located near an end of the tube 22 proximate the sample W. As shown in this example, the end of the tube 22 is sealed with the transmissive window 13. The transmissive window 13 should be uniformly transmissive across wavelengths, but if it is not, the transmission characteristics of the transmissive window 13 are taken into account for the design of the system 10 and in particular the MOE 48. This embodiment may include an additional focusing lens 66, which can be solid or have one or more apertures as shown in FIG. 1. The additional focusing lens 66 is used to focus or collimate a carrier light 46, described below, in a direction of the tube 22.

As further shown in FIGS. 1 and 2, the focusing lens 26 focuses the reflected light 44 onto, into or near the sample W via the transmissive window 13. In this example, the reflected light 44 is focused with a focal point 0-5 mm into the sample W. In addition to isolating components of the optical analysis system 10 from an external environment, the transmissive window 13 further enables a mixing vessel or container C, which is being tested/sampled into, to remain intact. As shown in this example, a one-inch (inner diameter) Swagelok® brand connector 62, available from Swagelok Corporation, Solon, Ohio, is used to connect the optical analysis system 10 to the mixing vessel C. This arrangement permits the reflected light 44 to be sent down the tube 22 (inner region 42A), interact with the material of interest W, reflect back up the tube 22 (outer region 42B), and be directed to the detectors 30, 32 as further described below.

As most clearly shown in FIG. 2, a tube 58 defines an aperture 60 for passage of the light signal 34 in a direction of the turning mirror 24. Separation of the illumination and reflection light paths or signals 44, 46 can be further defined or separated by physically separating the inner and outer regions 42A, 42B employing the tube 58. Any minimal reduction in light return of the carrier light 46 described below (caused by physical occupation of a portion of the outer region 42B by the tube 58) is offset by improvement in the amount of backscattered radiation returned to the detectors 30, 32 without encountering the sample W.

More specifically, the tube 58 is used to reduce a non-zero background measurement. The non-zero background measurement can occur in an optical system when a small amount of scattered light is returned to a detector even when no sample is present. Some of the scattered light can be reflected from a window, and some can come from the lenses themselves.

FIG. 2 shows that the tube 58 placed around the mirror 24 before the lens 26. The tube 58 reduces background signals by separating the excitation and collection light paths 34, 46 to minimize "cross-talk". As shown, the tube 58 defines an aperture 60 for passage of the light signal 34 in a direction of the turning mirror 24. As further shown, a conical extension 58A of the tube 58 can be placed after the mirror 24 in a direction of the detector 30. A thickness of the tube 58 should be minimized.

Also shown in FIG. 2, the tube 58 can have specular interior and exterior surfaces as well as a highly reflective coating 58B, such as gold, applied by electrolysis deposition, evaporation or other thin film coating method. The coating 58B reflects rays 34, 46 that would ordinarily terminate at a surface of the tube 58 back into respective optical paths from which they came. An image of the illumination source 14A, 14B may be vignetted, but the "lost" light in the image is still focused to a spot within the zone illuminated by the illumination source 14A, 14B. Likewise, the returning light outside the tube 58 can be kept from being lost by traveling inside an outer tube with a specular reflecting surface (not shown, but surrounding the outer light path). This will keep light loss to a minimum while keeping the input and output paths relatively isolated from one another.

As introduced above, the reflected light 46 shown in FIGS. 1 and 2 travels back down the outer annular region 42A of the sampling tube 22, past the turning mirror 24. The light 46 reaches the beam splitter 28 (one of its operating positions shown in phantom). The beam splitter 28 divides the light 46 with a neutral or gray spectrum, sending some of the light 46 in a direction of the first or Multivariate Optical Element (MOE) detector 30 through the MOE 48, briefly introduced above, and through a first lens 50 onto the photo detector 52, also briefly introduced above. The beam splitter 28 sends some other portion of the light 46 through a second lens 54 onto the other detector 56, also briefly introduced above.

As shown in the following table by example but not of limitation, some detectors suitable for use as the detectors 52,56 include:

TABLE 2

| Detector | Types[1] | Wave Range ($\lambda\mu$) | Detectivity $D^2$ | Cut Off Frequency ($H_z$) | Operating Temperature (K) |
|---|---|---|---|---|---|
| Pt—S | PV | 0.35-0.6 | 30 | $10^8$ | 295.0 |
| Si p-n PD | PV | 0.4-1.0 | 50 | $10^7$ | 295.0 |
| Si p-i-n PD | PV | 0.4-1.1 | 80 | $10^8$ | 295.0 |
| Si APD | PV | 0.4-0.8 | 80 | $10^{10}$ | 295.0 |
| Ge p-n PD | PV | 0.6-1.8 | 50 | $10^7$ | 295.0 |
| InSb p-n PD | PV | 3.0-6.2 | 8 | $5 \times 10^2$ | 77.0 |
| PbSnTe p-n PD | PV | 5.0-11.4 | >15-60 V/W | 10 | 77.0 |
| PbS | PC | 0.5-3.8 | 15.00 | 300 | 196.0 |
| PbSe | PC | 0.8-4.6 | 3.00 | $3 \times 10^3$ | 196.0 |
| PbTe | PC | 0.8-5.5 | 0.16 | $3 \times 10^3$ | 196.0 |
| p-InSb | PC | 2.0-6.7 | 2.00 | $2 \times 10^5$ | 77.0 |
| n-InSb | PC | 1.0-3.6 | 30.00 | $2 \times 10^6$ | 195.0 |
| PbSnTe | PC | 5.0-11.0 | 1.7 | $8 \times 10^5$ | 4.2 |
| CdHgTe | PC | 5.0-16.0 | 3.00 | $10^4$ | 4.2 |
| Ge: Au | PC | 2.0-9.5 | 0.02 | $10^4$ | 77.0 |
| Ge: Zn, Au | PC | 5.0-40.0 | 1.00 | $10^3$ | 4.2 |
| Ge: Cu | PC | 5.0-30.0 | 3.00 | $10^3$ | 4.2 |
| Si: Al | PC | 2.0-16.0 | 1.00 | $10^4$ | 27.0 |
| Si: Sb | PC | 2.0-31.5 | 1.80 | $10^4$ | 4.0 |
| ATGS | TC | 1-1000 | 0.030 | 10 | 295.0 |
| (Ba, Sr)TiO$_3$ | TC | 1-1000 | 0.011 | 400 | 295.0 |
| Si | — | 0.2-1.1 | — | — | — |
| Ge | — | 0.4-1.8 | — | — | — |
| InAs | — | 1.0-3.8 | — | — | — |
| InGaAs | — | 0.8-3.0 | — | — | — |
| InSb | — | 1.0-7.0 | — | — | — |
| InSb (77K) | — | 1.0-5.6 | — | — | — |
| HgCdTe (77K) | — | 1.0-25.0 | — | — | — |

Note 1:
PV—photo transistor type; PC: photo conductive detector type; TC: pyroelectric detector type Note 2:
($10^{10}$ cmHz$^{1/2}$ W$^1$)

As further shown in FIG. 1, a gain mechanism 64 is in communication with the detectors 30, 32 and the MOE 48. The gain mechanism 64 weights a magnitude of the property of an orthogonal component of a portion of the carrier light 48 as described, for instance, by Myrick et al. in U.S. Pat. No. 6,198,531 B1 and in U.S. Pat. No. 6,529,276 B1 to Myrick.

As briefly introduced above, the beam splitter 28 is not required in an alternative embodiment of the invention in which a signal from the sample W is analyzed using a PCR-type model in an off-line approach. This alternative embodiment and approach is useful, for instance, for studying signals independently. More particularly, a system substantially as described above but without the beam splitter 28 is used to take an integral of the light on a detector similar to the detector 30 described above. By analyzing frequency-dependent intensities, results similar to those of the foregoing embodiment are produced, although possibly with a relatively slower response time in the present embodiment.

Also, in an additional aspect of the invention as shown in FIG. 1, a system 68 using an electrochemical or chemometric model can be employed in conjunction with any of the foregoing embodiments to make similar or same measurements of the light 46 reflected from the sample W as the measurements described in the foregoing embodiments. By way of example but not of limitation, the system 68 may be one as described by Myrick et al. in PCT Application Number PCT/US2004/043742, based on U.S. Provisional Application No. 60/533,570, filed Dec. 31, 2003, which are incorporated herein by reference to these applications.

In addition to the reflectance mode described above, one or more optical analysis systems can operate in a transmission mode in conjunction with the foregoing embodiments. In such a case, light is directed (passes) through the sample W, e.g., a fluid sample, and collected on another side of the sample W to enable study of particle density in the fluid in conjunction with the chemical content described above. For instance, the system 10 can be configured to operate in transmission mode where the light is shone through the sample W to a similar detection system 110 as shown in FIG. 1 in phantom for clarity). Additionally, or alternatively, a mirrored surface 210 can be placed within the transmissive sample W to reflect the light back into the system 10.

Figure 3:
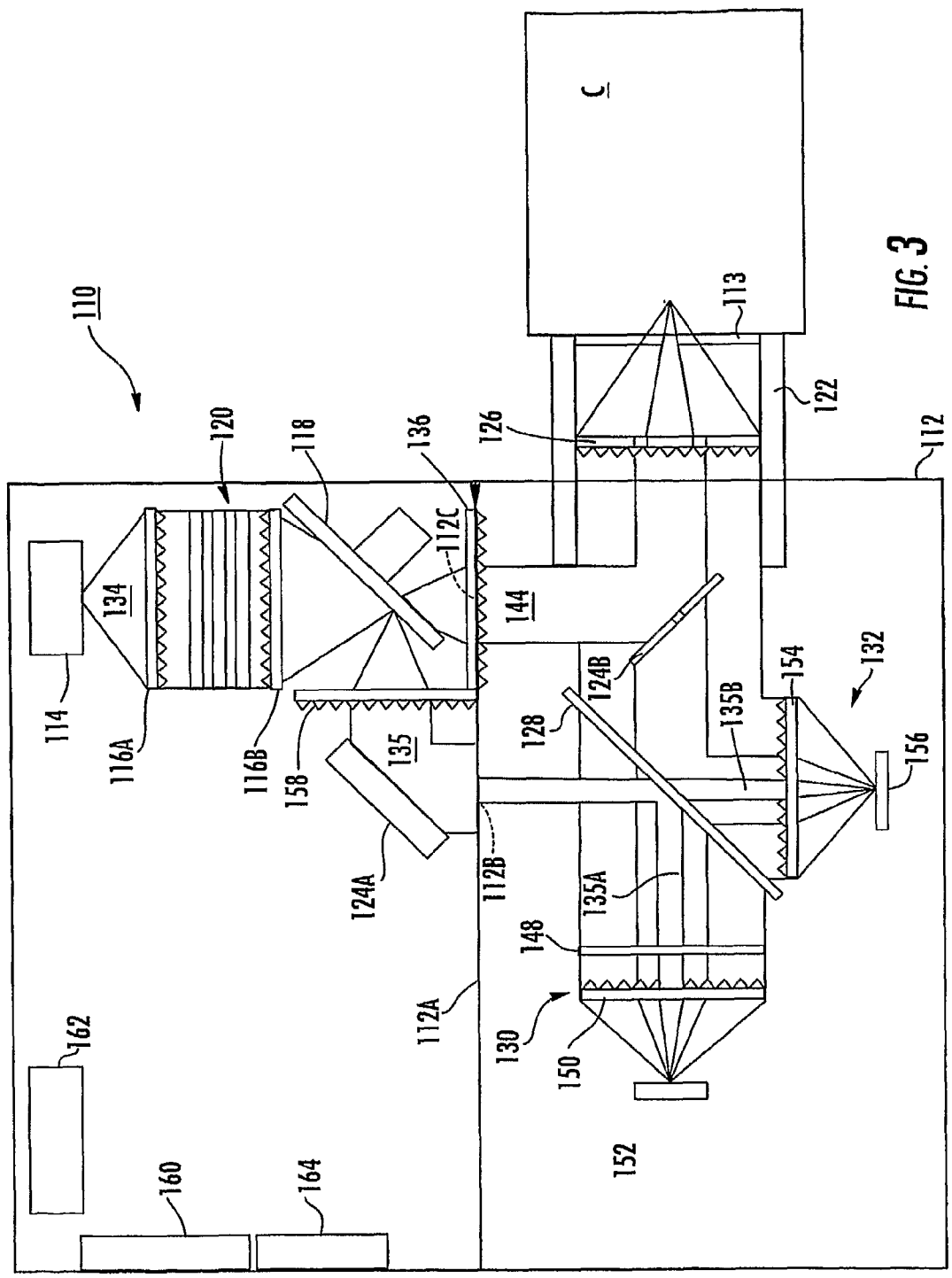
FIG. 3 is schematic plan view of another embodiment of a real time measurement system according to another aspect of the present invention.

With reference now to FIG. 3, a second exemplary embodiment of the present subject matter is designated generally by reference number 110. Many aspects of the optical analysis system 110 and related components are similar to the foregoing embodiment; thus, for the sake of brevity, only certain differences are described below. However, to provide a full and enabling disclosure of the optical analysis system 110, when like or similar elements and components are not specifically described below; implicit reference is made to the foregoing descriptions.

As shown in FIG. 3, the optical analysis system 110 broadly includes a housing 112, an illumination or light source 114, a chopper wheel 118, one or more spectral elements 120, a focusing lens 126, a beam splitter 128, a first detector 130 including a multivariate optical element 148, and a second detector 132. The optical analysis system 110 further includes an electrical connection 160, a pressurization sensor 162 and a purge gas assembly 164, which those skilled in the art will readily understand; therefore, further description is not necessary to understand and practice these aspects of the invention.

With more particular reference to FIG. 3, the illumination source 114 provides a light 134, which passes through a collecting Fresnel lens 116A and into and through the spectral element(s) 120. In this example, the illumination source 114 is rated for at least about 10,000 hours of operation, which alleviates a need for redundant illumination sources though they may be provided if desired. Also in this example, the collecting Fresnel lens 116A is sized to be about 1.5 square inches and is spaced about 0.6 inches from the illumination source 114. The skilled artisan will instantly recognize that these dimensions can be adjusted according to particular system requirements and are not meant as limitations of the invention.

As further shown in FIG. 3, the light 134 passes through the spectral elements 120, which filter out undesired wavelengths to define a desired spectral region, e.g., 1500-2000 nm, in order to target a particular chemical material of interest. The light 134 is focused by focusing Fresnel lens 116B, which is also sized to be about 1.5 square inches and spaced about 1 inch from the chopper wheel 118. As shown, the chopper wheel 118 reflects a portion of light 134 as a calibration or reference light 135 and a transmitted light 144. Calibration light 135 is collimated by lens 158 before reflecting from a first mirror 124A through an adjustable aperture 112B in a bulkhead 112A of the housing 112. The aperture 112B is adjustable to dictate a desired amount of the calibration light 135. Finally, calibration light 135 impinges on beam splitter 128 thereby sending a portion 135A of calibration light 135 to the first MOE detector 130 and a portion 135B of calibration light 135 to the second or baseline detector 132. FIG. 3 further illustrates that transmitted light 144 passes from the chopper wheel 118 into a collimating Fresnel lens 136, which in this example is sized to be about 1.5 square inches and is spaced about 0.6 inches from the chopper wheel 118. The transmitted light 144 passes through another adjustable aperture 112C in the bulkhead 112A and impinges upon a second mirror 124B, which directs the transmitted light 144 toward a sample in a container C, such as mixing vat or blender. The skilled artisan will recognize that the container could be a conveyor belt or other device for holding or transporting the sample and is not limited to an enclosed container.

As shown in FIG. 3, the transmitted light 144 is focused by the focusing Fresnel lens 126, which in this example may be round and about $15/16$ inches in diameter and is adjustable with an inner tube 122. Also in this example, lens 126 may be positioned about 0.6 inches from an outer surface of the container C. As shown, the transmitted light 144, now focused, passes through a transmissive window 113, which in this example is approximately 1 inch in diameter and with an anti-reflective (AR) coating disposed on one or both sides of the lens 126. The AR coating ensures that the chemical process in the container C does not interfere with the measuring process of optical analysis system 110. Thus, the transmitted light 144 enters the container C and reflects from the sample as a carrier light 146. The sample can be a moving mixture such as aspirin and an excipient being blended in real time, or a plurality of tablets passing by on a conveyor belt at high speed.

FIG. 3 further illustrates that the carrier light 146 is directed by the tube 122 in a direction of the first detector 130. Eventually, the carrier light 146 impinges on the beam splitter 128 and a portion passes in a direction of the detector 132 for baselining with the portion 135B of the calibration light 135. Another portion of the carrier light 146 passes through MOE 148, which as noted above, has been selected for the chemical of interest based on the various components of the system 110. Finally, that portion of the carrier light 146, having passed through the MOE 148, is focused by lens 150 and received by the detector 152. As described above, the two signals collected by the detectors 132 and 152 can be manipulated, e.g., mathematically, to extract and ascertain information about the sample carried by the carrier light 146.

Figure 4A:
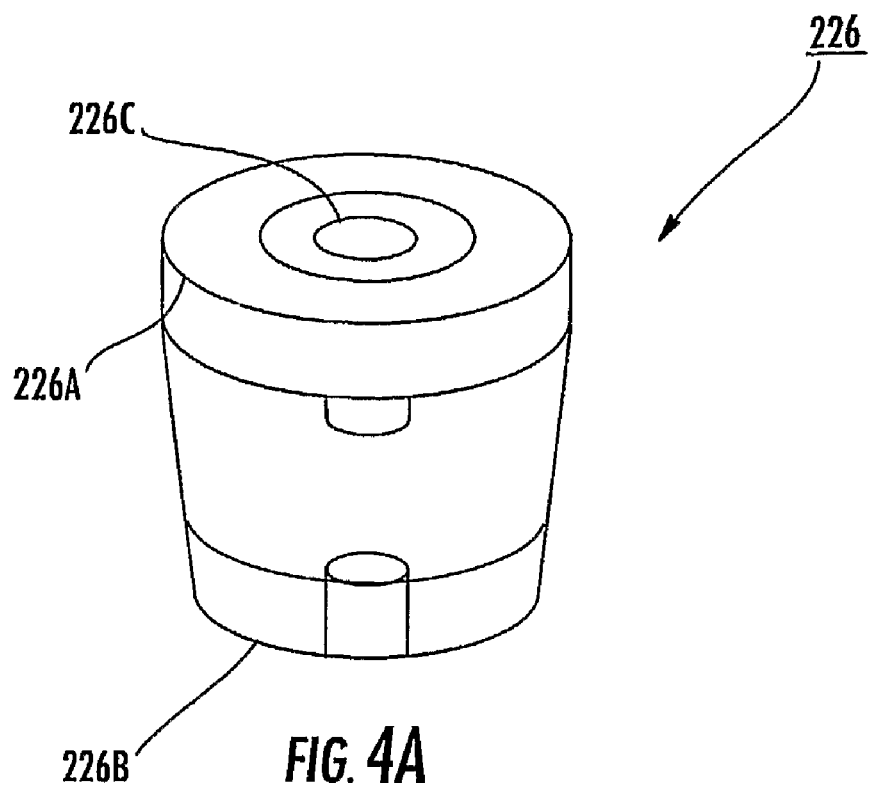
FIG. 4A is a perspective view of a retroreflecting mirror for use in the embodiments of FIGS. 1-3 according to a further aspect of the invention.
Figure 4B:
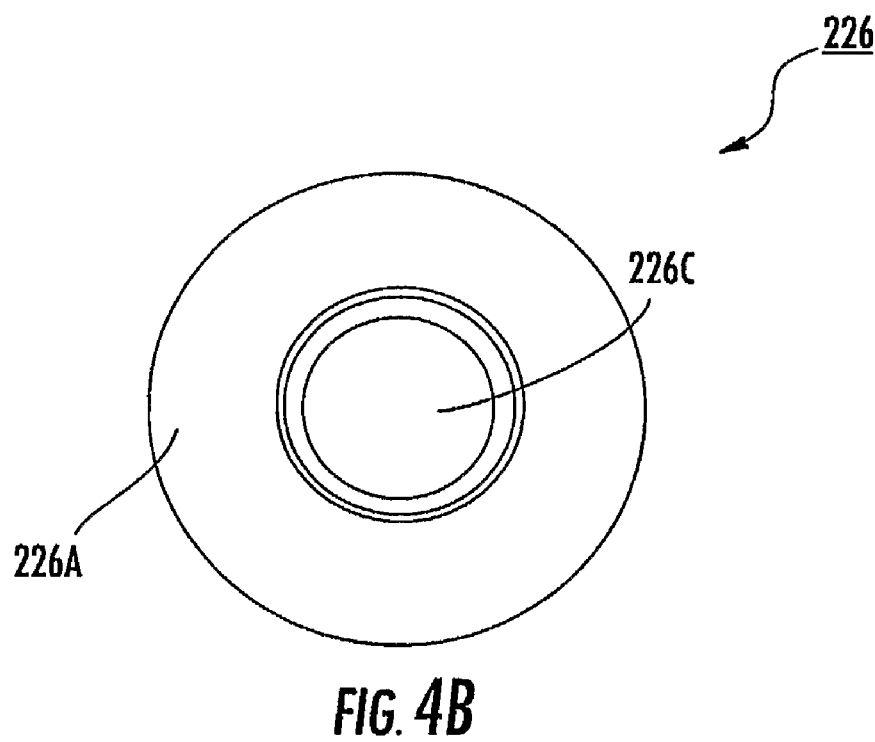
FIG. 4B is an end view of the retroreflecting mirror as in FIG. 4A.

Turning now to FIGS. 4A and 4B, detailed views of a collimating mirror 226 are shown. In this example, the mirror 226 has a first end 226A and a second end 226B and is generally cylindrically shaped. The mirror 226 is also coated with a reflective surface such as aluminum (Al), Au or other elements dictated by the desired spectral region. The skilled artisan will appreciate that other shapes and reflective coatings can be provided to meet specific design requirements and characteristics of the target sample; thus, the mirror 226 is not limited to the exemplary embodiment shown in FIGS. 4A and 413.

With reference to FIGS. 3, 4A and 4B, the mirror 226 is useful for analyzing translucent, liquid samples, for example, since liquids, in contrast to powders, do not readily create a diffuse reflectance to produce the desired carrier light 146 as shown in FIG. 3. By way of example operation, the lens 126 in FIG. 3 may be removed and replaced with the mirror 226 for liquid sample analysis. Accordingly, as the light 144 passes through the mirror 226, the light 144 is collimated into the liquid sample in the container C. The carrier light 146 reflects from the liquid sample and returns through the first end 226A, which defines a conical shaped depression or indentation 226C. The conical shaped indentation 226C acts to diffuse the carrier light 146 in a manner similar to the example shown in FIG. 3. Accordingly, a portion of the carrier light 146 is directed through the MOE 148 as described above. Again, the skilled artisan will appreciate that the invention is not limited to this exemplary arrangement. For example, the system can be arranged with the mirror 226 and the detectors 152, 156 on an opposing side of the container C such that the light 146 passes through the liquid sample into the mirror 226.

Dynamic Real-Time Detection and Measurement

The functionality of the MOC system 10 or 110 as described above allows for the collection of the entire spectral range of testing simultaneously. This fact is notably different than either a system based on either a scanning lamp or detector system or a discrete diode array detection system. The ability to monitor over the complete spectral range of interest opens up a re-definition of the term "real-time" measurement and analysis.

For instance, true real-time process measurements are possible. "Real time" refers to obtaining data without delays attendant to collecting samples or delays due to lengthy computer processing of measurement signals. In embodiments disclosed herein, process data can be obtained in an instantaneous or near-instantaneous manner through using the disclosed measurement techniques to directly monitor materials of interest while such materials are undergoing process steps. Long delays due to processing of measurement signals are avoided by optically processing the light as it is reflected from the material(s) of interest.

Although specific examples disclosed herein present monitoring the blending of a powdered material and examining solid tablets, the general concept can be extended to other phases. The present system can be utilized in analyzing solids, solutions, emulsions, gases, and dispersions, for example. In addition, while exemplary embodiments discussed herein use reflectance measurements, measurements in a transmission mode would also be an appropriate method.

One of ordinary skill in the art will recognize that differing applications may require modifications and alterations to certain components in order to take full advantage of the presently-disclosed systems. For instance, more diffusion of light has been observed in solid powders relative to liquids; accordingly, different lenses may be needed when a liquid is monitored in order to account for such variations and achieve more accurate measurements.

The presently-disclosed technology can be applied to real-time measurements for a range of industrial applications. These include, but are not limited to monitoring of the blending of pharmaceutical powders, including excipients, additives, and active pharmaceutical materials; blending of other powders, including food and chemicals; monitoring dispersions and bi-phasic mixtures (such as insulin, emulsions); and oil and gas applications, including analyzing water content in oil, or oil content in water.

Inclusion of a transmissive window into a closed system allows for in-line measurement and/or non-invasive measurement of parameters such as chemical functionality, including alcohol content of petroleum fractions or tackifier resins. Environmental applications are also conceivable, such as stack gas analysis, including measurement of NOx, SOx, CO, CO2, or other gases in a gas stream; wastewater analysis and treatment monitoring; and hazardous substance monitoring applications such as mercury vapor detection.

Real Time Measurement of Powder Mixing

As noted above, MOC technology can be used to monitor a wide variety of materials as the materials are subjected to different processes. For instance, the mixing of powders can be monitored. As materials are blended, the existing art does not allow for continuous, real-time, in-line measurement. Current limitations are the result of several factors including: moving of the powders being measured during the course of data acquisition and the need to connect analytical equipment to the measurement point using fiber optic cables. This optical analysis system is designed to allow for instantaneous measurement using a measurement point located on the vessel.

Figure 6:
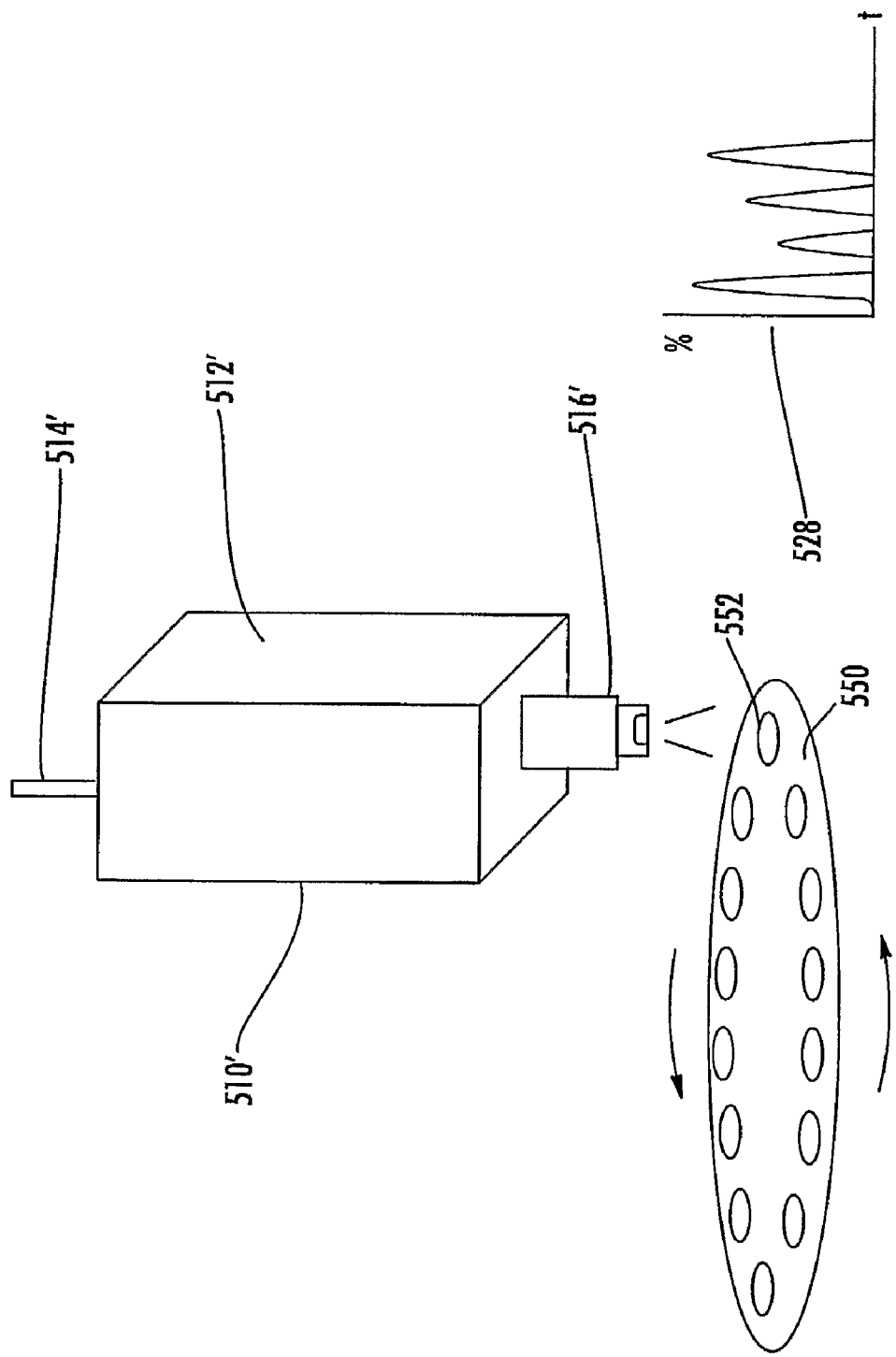
FIG. 6 is another schematic view of a real-time process measurement using the present invention.

To measure the composition of the mixture of powders during blending, the system is located in a position to shine the sampling beam into the mixture. An exemplary implementation of such a measurement technique is illustrated in FIG. 6. Optic head 510 includes housing 512, requisite MOEs and spectral elements to obtain desired information about the material of interest, and is generally configured and constructed in accordance with the embodiments discussed above in conjunction with FIGS. 1-4.

In discussing various embodiments below, the term "optic head" is used in place of the term "measurement system" in referring to the light, lenses, spectral elements, and detectors of the optical computing unit discussed above. As will be apparent to one skilled in the art, a complete measurement system may utilize several instances of the optical computing unit, and so the term "optic head" is used as a shorthand reference to a single instance of the optical computing unit.

Optic head 510 is connected via umbilical 514 to an appropriate power supply and analysis computer or computers, also configured in accordance with the principles of multivariate optical computing analysis. A process point, in this illustration a mixing blender bowl 522 containing mixture 524, may thereby be monitored via optic head 510.

A port/connection 520, in one exemplary embodiment a Swagelok® brand pharmaceutical-grade stainless steel port (available from Swagelok of Solon, Ohio), connects the opening 518 of mixing blender bowl 522 therein to optic head inlet 516. Inlet 516 includes the window (13 or 113 in the embodiments discussed above) through which light is transmitted and reflected for materials analysis while keeping the material monitored separate from the internal components of the optic head.

In one embodiment, an optic head can be configured to monitor the concentration of a mixture of aspirin and lactose. A sapphire window is located at the end of optic inlet 516 for interrogating the powder, and the optic head is configured with multivariate optical elements designed to monitor aspirin concentration. A 20-watt Gilway lamp is modulated using 5 mm D2O and 5 mm Germanium spectral elements, and the modulated light is directed into the powder. The reflected light from the powder is directed through the multivariate optical elements onto a PbS detector. A portion of the modulated light, as discussed above, is preferably directed into a second detector. The resulting PbS detector signal can be compared against the second detector signal in order to determine the concentration of aspirin.

Figure 5:
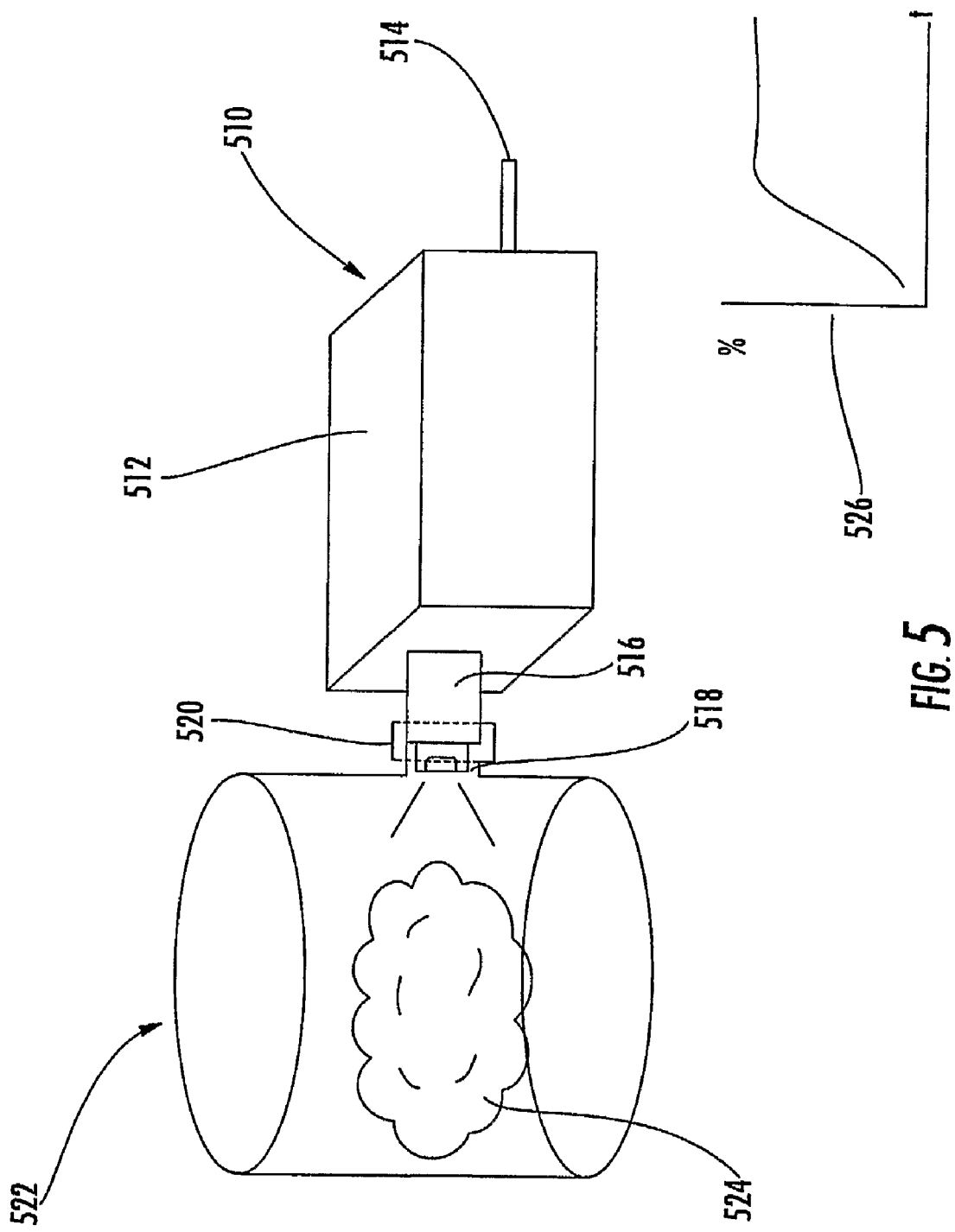
FIG. 5 is a schematic view of an implementation in which material(s) undergoing a process step may be measured in real-time using the present invention.

For instance, a concentration graph such as that illustrated at 526 in FIG. 5 may be obtained, showing the rise in aspirin concentration as it is added and the leveling-off as the mixing process continues.

Embodiments in which transmitted light is measured would utilize two ports, preferably located opposite one another with the measured sample passing between the two ports.

Real Time Measurement of Chemicals/Flowing Materials

Other embodiments of the present invention include real time measurement of flowing materials. In such embodiments, the sampling window(s) may be located on a pipe or vessel such that interrogating illumination can be applied to the material. For instance, a port similar to port 520 in FIG. 5 could be included on a pipe to allow for sampling of the material inside the pipe. The window may be positioned directly on the pipe, or on a small diversion away from the main flow path, as appropriate under the circumstances. Such embodiments could also include sampling of vapor systems within a stack to monitor combustion gases or flowing process stream such as water containing other materials.

Real Time Measurement of Moving Containers

Still further embodiments of the present invention include the real time measurement of materials in containers, such as vials or bins where the container is either at least partially open to the outside environment or transmissive to the sampling illumination. Such containers could be stationary or in motion. A container could also include a conveyor or trough carrying material. Typical applications could include the monitoring the progress of a chemical reaction or the content of samples moving past a measurement location.

For instance, FIG. 6 illustrates a plurality of samples 552 positioned on a rotating disc conveyor 550. One of ordinary skill in the art will recognize that the samples may be positioned on a conveyor belt or moved using another automated conveyance, depending upon the particular testing circumstances and environment. The samples 552 are illustrated as tablets in FIG. 6, which could include capsules, caplets, pills, and other individualized units of pharmaceutical (or other) product.

As shown in FIG. 6, tablets 552 are rotated into the view of optical inlet 516' for optic head 510', which as discussed earlier, includes housing 512' and umbilical 514', as well as requisite internal components, filters, and MOEs to perform the desired testing operations. Embodiments of the present invention may be configured to monitor around 5 tablets per second, with the tablets in continuous motion.

As discussed in conjunction with the optic head of FIG. 5, in one embodiment, a PbS detector can be used in conjunction with a sapphire window and D20 and germanium spectral elements to monitor the concentration of aspirin and lactose. Unlike the system in FIG. 5, the sapphire window of the optic inlet 516 is positioned above the samples such that the beam of light is focused downward onto the samples on the conveyor belt. However, the optical principles remain the same. Graph 528 represents exemplary results that would be obtained by samples of varying concentration of aspirin, with each spike representing when a sample is in full view of the optic head 510'.

Samples 552 may comprise the actual samples to be measured, such as the tablet end-product illustrated in FIG. 6 and discussed below in conjunction with FIG. 7. However, one of ordinary skill in the art will recognize that samples 552 may also comprise transparent containers and the like, which may contain a dispersion or suspension of a solid material in a liquid or a solution, or solid materials. For instance, trays of powder can be placed on an automated conveyance and brought into view of optic head 510' in a similar manner.

Instead of moving samples 552, one of ordinary skill in the art will note that measurement device 510' could be repositioned to examine the samples 552 by appropriate machinery such as overhead tracks, robotic arms, and the like. The skilled artisan will recognize that in such cases, appropriate care would preferably be taken to ensure that force levels applied to the measurement device and its internal components remained within tolerable levels.

Integrated Real-Time Process Management Using MOC Systems

Figure 7:
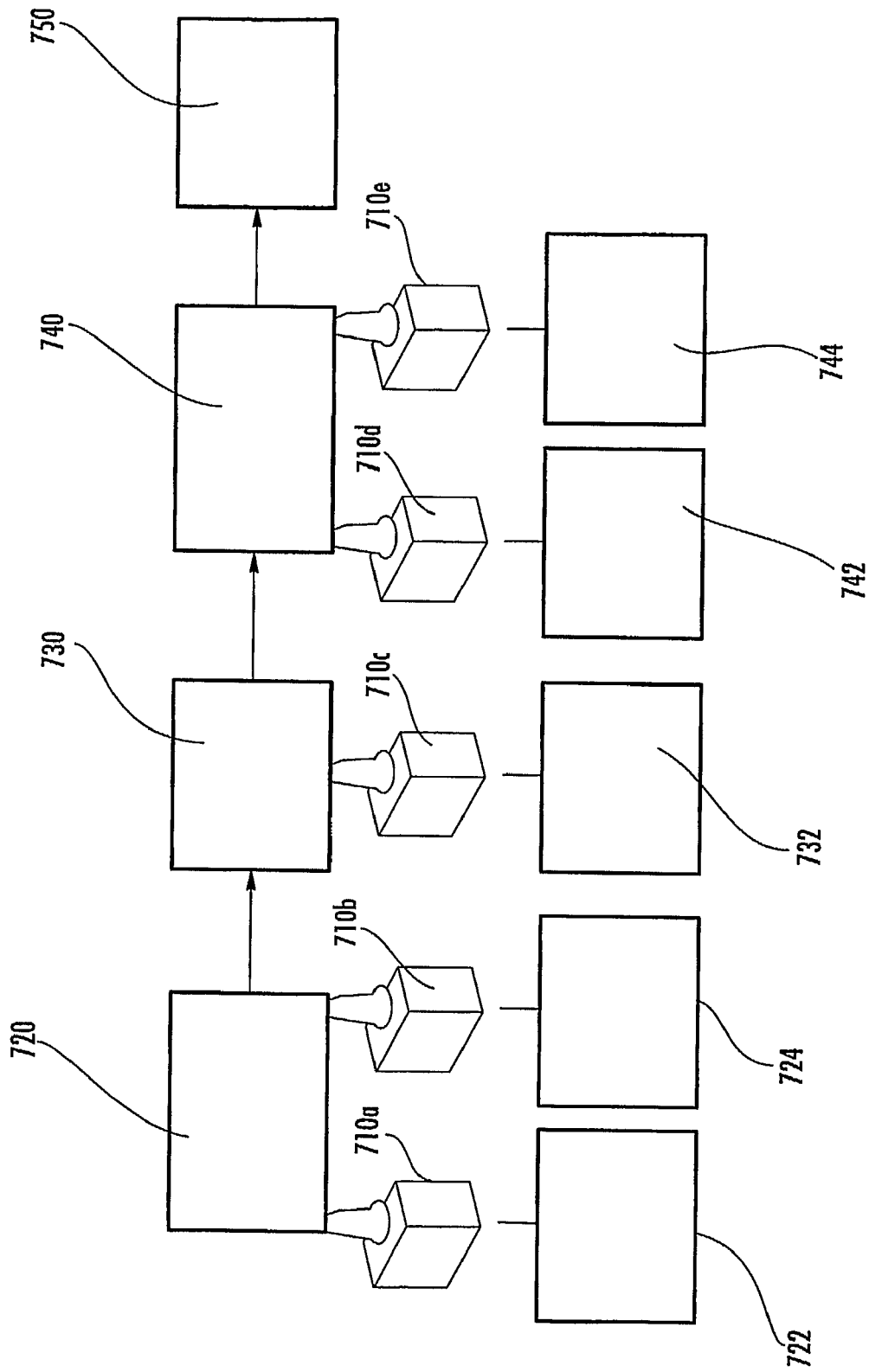
FIG. 7 is a schematic view of using the present invention at multiple process stages to monitor material characteristics.

An illustration of one embodiment of real-time process management is found in FIG. 7. A plurality of optic heads 710 are shown integrated into various process steps 720, 730, and 740. Process steps 720, 730, and 740 can represent stages or steps of any number of industrial operations in which materials are handled or manipulated, and in which physical state or compositional data is desirable. In accordance with the system embodiments discussed above, each optic head 710a, b, c, d, e is provided with MOEs and other optical components specifically tailored to the materials characteristics which are to be monitored at each step, and interfaced with the process control computer(s). The analysis data ultimately provided by collection points 710 is shown at 722, 724, 732, 742, and 744. Such data can be obtained using single or multiple process control computers configured to collect, analyze, and otherwise handle the data from the detectors within the optic heads in accordance with the principles of multivariate optical computing discussed above.

Assume, for example, that process steps 720, 730, and 740 represent various stages in a pharmaceutical manufacturer's production line for blending powder and forming tablets. The skilled artisan will recognize that pharmaceutical manufacturing often entails strict control and monitoring of material composition and mixing at every stage of production.

The initial steps of obtaining and readying component materials in a pharmaceutical process could be represented at 720. Optic head 710a could be used to monitor the incoming raw materials in trays or on conveyors and provide inspection and quantification data 712, such as purity data. Optic head 710b could be configured to the monitor incoming material(s) as they undergo an initial process stage, for example, providing chemical drying characteristics 724 as the raw materials are dried.

Process step 730 could represent mixing of active and excipient components into a powder, and optic head 710c could provide data 732 on mixing progress. For instance, optic head 710c could be interfaced with the mixing container and provide data tracking active ingredient concentration over time as shown in FIG. 5. Based on such concentration, requisite steps could be taken to ensure the optimal amount of active component is in the resulting mix or otherwise adjust the mixing process by altering temperature or the like.

Step 740 could represent pressing tablets, with optic heads 710d and 710e positioned above a conveyor moving the completed tablets, and providing data 742 on tablet components and homogeneity, and data on coating thickness and uniformity 744.

Step 750 represents the final portions of the manufacturing process which are not monitored, such as packaging. One skilled in the art will, of course, recognize that step 750 could represent the entry into a different process which is itself monitored by one or more optical analysis systems.

The invention may be better understood from the following tests and examples.

Example I

System I

A first breadboard system was constructed and used to test a mixture of powders.
System I components:
Illumination: 20 W Gilway lamp
Spectral elements: 5 mm deuterium oxide ($D_2O$), 5 mm Germanium
Optical window: fiber optic probe
Detector: InAr detector from Judson
MOE: specific to test
Procedure and Results of Static Testing Using System I:
A powdered sample with a known composition was placed in a dish and the fiber optic probe was placed in contact with the powder. The output of the detectors was monitored and recorded.

Example II

System II

A system similar to the optical analysis system 10 shown in the figures was constructed and used to make static measurements on aspirin/lactose.
System II Components:
Illumination: 20 W Gilway lamp
Spectral elements: 5 mm D2O, 5 mm Germanium
Optical window: none
Detector: PbS detector from New England Photoconductor
MOE: specific to test conditions.

Procedure and Results of Static Testing using System II:

A powdered sample with a known composition was placed in a dish and the system light beam was focused on the powder. The output of the detectors was monitored and recorded. Aspirin/lactose samples covering the range of 100% aspirin to 100% lactose were tested.

Example III

System III

A system similar to the optical analysis system 10 shown in the figures was constructed and used to make dynamic measurements on aspirin/lactose.
System III Components:
Illumination: 20 W Gilway lamp
Spectral elements: 5 mm D2O, 5 mm Germanium
Optical window: sapphire window
Detector: PbS detector from New England Photoconductor
MOE: specific to test conditions.
Procedure and Results of Dynamic Testing using System III:

The Aspirin/Lactose testing was made on a mixer bowl containing lactose and the system measured as aspirin was added to the system and mixed. Specifically, lactose powder was placed in the bowl of a mixer and the measurement system was attached the bowl using a Swagelok® brand fitting. A sapphire window was used to contain the powder in the bowl and allow the system to interrogate the powder. With the mixer turning, known amounts of aspirin were added and the system output signal was monitored and recorded. Aspirin was added in several allotments to about 37% final aspirin concentration.

Example IV

System IV

A system similar to the optical analysis system 10 shown in the figures was constructed and used to make static measurements on aspirin/lactose.
System IV Components:
Illumination: 5 W Gilway lamp
Spectral elements: 5 mm D2O, 5 mm Germanium
Optical window: none
Detector: PbS detector from New England Photoconductor
MOE: specific to test conditions.
Procedure and Results of Dynamic Testing using System III:
Similar to the examples above.

Although the invention has been described in such a way as to provide an enabling disclosure for one skilled in the art to make and use the invention, it should be understood that the descriptive examples of the invention are not intended to limit the present invention to use only as shown in the figures. For instance, the housing 16 can be shaped as a square, an oval, or in a variety of other shapes. Further, a variety of light sources can be substituted for those described above. It is intended to claim all such changes and modifications as fall within the scope of the appended claims and their equivalents. Thus, while exemplary embodiments of the invention have been shown and described, those skilled in the art will recognize that changes and modifications may be made to the foregoing examples without departing from the scope and spirit of the invention.

That which is claimed is:

1. A method of real-time processing and monitoring, comprising:
   blending a material of interest with a secondary material;
   separating a source light into an illumination light and a calibration light;
   illuminating the blended materials with the illumination light;
   dividing light carrying information about the blended materials with a beam splitter into a first light portion and a second light portion, the first light portion and the second light portion having substantially similar characteristics;
   after dividing the light with the beam splitter, directing the first light portion through at least one multivariate optical element to produce a first signal;
   detecting the first signal at a first detector;
   directing the second light portion in a direction of a second detector, the second detector configured to detect the second light portion;
   detecting a portion of the calibration light at the first detector; and
   determining, in real time, at least one selected property of at least one of the blended materials based upon a first detector output and a second detector output.

2. The method as in claim 1, wherein real time is faster than 1/1000 of a second.

3. The method as in claim 1, wherein real time is faster than 1/100 of a second.

4. The method as in claim 1, wherein real time is faster than 1/10 of a second.

5. The method as in claim 1, wherein real time is faster than 1 second.

6. The method as in claim 1, wherein real time is faster than 5 seconds.

7. The method as in claim 1, wherein real time is faster than 30 seconds.

8. The method of claim 1 wherein the blending material of interest includes a gasoline and the at least one selected property is an octane rating.

9. A method of real-time pharmaceutical processing and monitoring, comprising:
   blending a pharmaceutical powder by mixing an active agent with an excipient;
   separating a source light into a spectral-specific light and a calibration light;
   illuminating the pharmaceutical powder with the spectral-specific light through an optic window, the optic window configured to focus the spectral-specific light into the pharmaceutical powder;
   dividing light carrying information about the pharmaceutical powder with a beam splitter into a first light portion and a second light portion, the first light portion and the second light portion having substantially similar spectral characteristics;
   after dividing the light with the beam splitter, directing the first light portion through at least one multivariate optical element to produce a first signal;
   detecting the first signal at a first detector;
   detecting a portion of the calibration light at the first detector;
   directing the second light portion in a direction of a second detector, the second detector configured to detect the second light portion; and
   determining, in real time, at least one selected property of the pharmaceutical powder based upon a first detector output and a second detector output.

10. The method as in claim 9, wherein the selected property of the pharmaceutical powder is an active property of the active agent.

11. The method as in claim 9, wherein the selected property of the pharmaceutical powder is a particulate size of the active agent.

12. The method as in claim 9, wherein the selected property of the pharmaceutical powder is a secondary property of the excipient.

13. The method as in claim 9, further comprising assessing an homogeneity asymptote of the pharmaceutical powder.

14. The method as in claim 9, wherein real time is faster than $1/1000$ of a second.

15. The method as in claim 9, wherein real time is faster than $1/100$ of a second.

16. The method as in claim 9, wherein real time is faster than $1/10$ of a second.

17. The method as in claim 9, wherein real time is faster than 1 second.

18. The method as in claim 9, wherein real time is faster than 5 seconds.

19. The method as in claim 9, wherein real time is faster than 30 seconds.

20. A method of real-time pharmaceutical processing and monitoring, comprising:
    separating a source light into a spectral-specific light and a calibration light;
    illuminating a fluid in a container with the spectral-specific light through an optic window disposed proximate an aperture in a conduit in communication with the container;
    dividing light carrying information about the fluid with a beam splitter into a first light portion and a second light portion, the first light portion and the second light portion having substantially similar spectral characteristics;
    after dividing the light with the beam splitter, directing the first light portion through at least one multivariate optical element to produce a first signal;
    detecting the first signal at a first detector;
    detecting a portion of the calibration light at the first detector;
    directing the second light portion in a direction of a second detector, the second detector configured to detect the second light portion; and
    determining, in real time, at least one selected property of the fluid as the fluid flows past the optic window, based on a first detector output and a second detector output.

21. The method as in claim 20, wherein the fluid is opaque in appearance.

22. The method as in claim 20, wherein the fluid is a liquid chemical and the window is configured to focus the spectral-specific light into the liquid chemical.

23. The method as in claim 22, wherein the liquid chemical is a blend of at least one active pharmaceutical agent and at least one excipient.

24. The method as in claim 20, wherein the fluid is a gas.

25. The method as in claim 24, wherein the gas is opaque in appearance.

26. The method as in claim 20, wherein real time is between about $1/1000$ of a second to about 30 seconds.

27. A method of real-time processing and monitoring, comprising:
    mixing a material of interest with a secondary material;
    separating a source light into an illumination light and a calibration light;
    illuminating the materials with the illumination light;
    dividing light carrying information about the materials with a beam splitter into a first light portion and a second light portion, the first light portion and the second light portion having substantially similar spectral characteristics;
    after dividing the light with a beam splitter, directing the first light portion through at least one multivariate optical element to produce a first signal;
    detecting the first signal at a first detector;
    detecting a portion of the calibration light at the first detector;
    directing the second light portion in a direction of a second detector, the second detector configured to detect the deflected portion; and
    determining, in real time, at least one selected property of at least one of the materials, based upon a first detector output and a second detector output.

28. The method as in claim 27, wherein the selected property is determined based upon a compositional change.

29. The method as in claim 28, wherein the compositional change includes a chemical reaction.

30. The method as in claim 28, wherein the compositional change includes a crystallization process.

* * * * *